United States Patent
Bougueleret

(10) Patent No.: US 6,472,517 B1
(45) Date of Patent: Oct. 29, 2002

(54) NUCLEIC ACIDS ENCODING HUMAN CIDE-B PROTEIN AND POLYMORPHIC MARKERS THEREOF

(75) Inventor: Lydie Bougueleret, Petit Lancy (CH)

(73) Assignee: Genset S.A., Paris (FR)

(*) Notice: Subject to any disclaimer, the term of this patent is extended or adjusted under 35 U.S.C. 154(b) by 0 days.

(21) Appl. No.: 09/807,166

(22) PCT Filed: Oct. 8, 1999

(86) PCT No.: PCT/IB89/01702

§ 371 (c)(1),
(2), (4) Date: Sep. 10, 2001

(87) PCT Pub. No.: WO00/21984

PCT Pub. Date: Apr. 20, 2000

Related U.S. Application Data

(60) Provisional application No. 60/103,729, filed on Oct. 9, 1998.

(51) Int. Cl.[7] .......................... C07H 21/02; C07H 21/04
(52) U.S. Cl. ................. 536/23.5; 536/23.1; 536/24.31; 536/24.1; 536/24.2
(58) Field of Search .................. 435/6, 91.2; 536/21.3, 536/24.1, 24.2, 24.31, 23.5

(56) References Cited

FOREIGN PATENT DOCUMENTS

| WO | WO 93/16178 | * | 8/1993 |
| WO | WO 99/55134 A2 | | 11/1999 |

OTHER PUBLICATIONS

Strausberg, R. National Center for Biotechnical Information, National Library of Medicine, NIH (Bethesda, MD, USA) 1998, Accession No. A1051238.*

Strausberg, R. National Center for Biotechnical Information, National Library of Medicine, NIH (Bethesda, MD, USA) 1997, Accession No. AA283696.*

Inohara, et al.; "CIDE, a novel family of cell death activators with homology to the 45 kDa subunit of the DNA fragmentation factor"; The EMBO Journal, vol. 17, No. 9, pp. 2526–2533, 1998; XP–002133431; Oxford University Press.

Inohara, et al.; "CIDE, a novel family of cell death activators with homology to the 45 kDa subunit fo the DNA fragmentation factor"; The EMBO Journal, vol. 17, No. 9, pp. 2526–2533, 1998; XP–000882759; Oxford University Press.

Database EMBL 'Online!; accession No. A1051238; Strausberg; "NCI/CGAP, tumor gene index: . . . similar to . . . cell death–inducing DNA fragmentation factor, alpha subunit––like effector B"; XP–002133432; abstract.

Database EMBL 'Online!; accession No. AW024578; Sep. 14, 1999; Strausberg; "NCI/CGAP, tumor gene index: . . . similar to . . . cell death–inducing DNA fragmentation factor, alpha subunit–like effector B."; XP–002133433; abstract.

Xiong, Etal.; "Biallelic markers in genetics studies of human diseases: their power, accuracy, and density in population––based linkage analyses"; American Journal of Human Genetics (Oct. 1997), vol. 61, No. 4, Suppl., pp. A301; 47th Annual Meeting of the American Society of Human Genetics, Baltimore, MD, XP–000852591.

Kruglyak, Leonid; "The use of a genetic map of biallelic markers in linkage studies"; Nature Genetics, vol. 17, Sep. 1977, p. 21–4; XP–000882279.

Database EMBL 'Online!; accession No. p56198/ID FS27__ mouse; Nov. 1, 1997; Danesch, et al.; "Fat–specific protein FSP27"; XP–002133434.

* cited by examiner

Primary Examiner—Carla J. Myers
(74) Attorney, Agent, or Firm—John Lucas; Carol Johns

(57) ABSTRACT

The present invention relates to a purified or isolated polynucleotide encoding human CIDE B protein, the regulatory nucleic acids contained therein, polymorphic markers thereof, and the resulting encoded protein, as well as to methods and kits for detecting this polynucleotide and this protein. The present invention also pertains to a polynucleotide carrying the natural regulatory regions of the CIDE B gene which is useful, for example, to express a heterologous nucleic acid in host cells or host organisms as well as functionally active regulatory polynucleotides derived from said regulatory regions.

68 Claims, 1 Drawing Sheet

```
                    SEQUENCE LISTING

<160> NUMBER OF SEQ ID NOS: 5

<210> SEQ ID NO 1
<211> LENGTH: 10961
<212> TYPE: DNA
<213> ORGANISM: Homo sapiens
<220> FEATURE:
<221> NAME/KEY: misc_feature
<222> LOCATION: 1..2802
<223> OTHER INFORMATION: 5' regulatory region
<221> NAME/KEY: exon
<222> LOCATION: 2803..2922
<223> OTHER INFORMATION: exon 1
<221> NAME/KEY: exon
<222> LOCATION: 3225..3369
<223> OTHER INFORMATION: exon 2
<221> NAME/KEY: exon
<222> LOCATION: 4217..4366
<223> OTHER INFORMATION: exon 3
```

```
<221> NAME/KEY: exon
<222> LOCATION: 4603..4793
<223> OTHER INFORMATION: exon 4
<221> NAME/KEY: exon
<222> LOCATION: 4975..5555
<223> OTHER INFORMATION: exon 5
<221> NAME/KEY: misc_feature
<222> LOCATION: 5556..10961
<223> OTHER INFORMATION: 3' regulatory region
<221> NAME/KEY: allele
<222> LOCATION: 7123
<223> OTHER INFORMATION: 12-73-49 : polymorphic base C or T
<221> NAME/KEY: allele
<222> LOCATION: 9574
<223> OTHER INFORMATION: 12-74-38 : polymorphic base C or T
<221> NAME/KEY: primer_bind
<222> LOCATION: 6704..6723
<223> OTHER INFORMATION: 12-73.rp
<221> NAME/KEY: primer_bind
<222> LOCATION: 7152..7169
<223> OTHER INFORMATION: 12-73.pu complement
<221> NAME/KEY: primer_bind
<222> LOCATION: 9538..9557
<223> OTHER INFORMATION: 12-74.pu
<221> NAME/KEY: primer_bind
<222> LOCATION: 9970..9988
<223> OTHER INFORMATION: 12-74.rp complement
<221> NAME/KEY: misc_binding
<222> LOCATION: 7100..7146
<223> OTHER INFORMATION: 12-73-49.probe
<221> NAME/KEY: misc_binding
<222> LOCATION: 9551..9597
<223> OTHER INFORMATION: 12-74-38.probe
<221> NAME/KEY: primer_bind
<222> LOCATION: 7104..7122
<223> OTHER INFORMATION: 12-73-49.mis
<221> NAME/KEY: primer_bind
<222> LOCATION: 7124..7142
<223> OTHER INFORMATION: 12-73-49.mis complement
<221> NAME/KEY: primer_bind
<222> LOCATION: 9555..9573
<223> OTHER INFORMATION: 12-74-38.mis
<221> NAME/KEY: primer_bind
<222> LOCATION: 9575..9593
<223> OTHER INFORMATION: 12-74-38.mis complement

<400> SEQUENCE: 1
ggctgtgcct gtggcccgcg aagtcttcca gctcagcagt gtctcgttcc ctggggacg      60 gtagcagacc gacatccttc tgggcctaca ggtgggtgga aggcgccaca gagggcgttc    120
aggggtgggg caaaacccca cctgtgatgc ccgatgagaa ggtgccatgc ctcctcctta    180
cttccctgca gcctgcctct tttctgcctg ggagtcctga cttccacgag acccagacc    240 ccacctcaaa cacaactcct tcttggaacc cagatcccct gctcccagtc agttgacctg    300
ccccactcct ggcctccttc ccagagctca gtggtaaaca ggcataaagt cctcacccca    360
ggctgtcact atctctacca ccactcctct agtctggccc ctccttcttt gtccagcccc    420
attctagcac atctgggcaa aactggatgg tggggtgtaa agggacgtgc acagatctac    480
ttaccaagct gggagcaagc aggattgggg gcctggagaa gctgaaaggt taagcagcag    540
taggcgaggt gcctactcct gtcctgtgcc tatcacattt gcagagggta agacaagaat    600
ggggagggac aagatgaggc tcatcctggg cctctcctgg ggcccctccc tcaccctgct    660
ccttcccatc accaacgcac ccaggcgtcc aggcatgtga gagcctgcct tgccaggaaa    720
cagcacaagc tgaagtgggg cagtaagatt ccctggtggt ggaaggaaat aggaggactc    780
tgctgaatcc tggtcctgct tctgttctca tccctccccc agctctggcc ccaatcctcc    840
cagcccacct tctgcagtgt gtatgttgcc tggtctctct ggcctgcaga ggtgacccaa    900
acaactcagt ccccccacctg ccttatcctt gcctgtttcc agtctcctgg tccggctgag    960
```

```
cccctggcct cctacctcct cccacctctt gcctcaggcc ctgccccagt cactccaccc    1020
tcagggctct caccgggctg tcaatgacag cttttccatg taaggcatgg tgctaggttc    1080
caggaggaac aggggatgca tggaggcata atggttaggg agtcatgaca cacaaccatg    1140
aagaggcccc attaccaggc tgcaccagga tacaagacaa gaaaggaaag gatgagtagg    1200
gacatactaa gaagcagccc tctcctcttg gaaaagtcaa gcaaaacttg gaaatgaaga    1260
gatttgaggg gggcctggca gatggataga gctggggaa gggaaaagaa aggcctctgc     1320
tcaagtaaca gccagaactt gaggttgctt ggggagggca ccaggagcac tgtcttagtt    1380
tgggttcttc caaagcagag cttgagctaa gggcttgggt acaggtgatc ctgtattctt    1440
gagctaaggg cttgggtaca ggtgatcctg tatttgggag gttaactcag gaagtgaggg    1500
cataaggtaa aacaagagag aggaaagcca ttaagagtat gttaagtccc ttcagtaggc    1560
cttgggaacc tctgagaaaa gtatagattg cccaagacaa aagactggca gggtgatcag    1620
tccaaagcat ttattaggag aatgtactta atgagtgggc tacagcgtat cctcacaaca    1680
gacagtgaga gagagttgtt ctacctgggt atatccaaaa caaggggtc agggtatgga     1740 gtttacgagg gttcaaggta tttggttcag ggccagggcc agttttttc agtgttttgg     1800 gcaacaacct gaatacctttt tcaaggctct ggcttgggct caagcctgca ggggaaatgc    1860
aactggccag gtcacagggc aatcaagtta ctctgtgttt ctttgtcagg acacagaaaa    1920
aaagtgggga agctgggggga ccctacaagg atccttggca ggaaagcagg gattgtgttc    1980
atttgagggt ttcactgtca gtgagagtct cagcttccat gcaactgtcc atcacggctg    2040
caactgaaat cagagctggg acacagcgca ccagaagcta aagtcttgat gccatcaaag    2100
gacatccctg ccccattcac atctctgtca cgtccactaa tcggcaaaag gagaaaagtg    2160
agagaagatg acctaagtgt gactgcagca ggcagctctg gaaatgaag ccagagcagt     2220 gagccagccc ctcctccgac caaggaggaa ggaaagagca ggtaagcagg aaggccagtg    2280
tcccagacag gaccctaatg atcctgaatc catgtatcag gatccatcct ctccttacac    2340
ccttcctgga cacactctca cctctcattt tccaaagccc tgccatgctg ccatcccact    2400
tccccacact ctgccccggg ttccctttc ctaaagctgc agcttatggc ttctccagta     2460
ggtggcagca cacacagagc cactcataaa ctgcagcttc tcagagcctg agagccagaa    2520
accgtcccca gaaagtccct ccatagaaat aaaaaaacac cagaagtcac atttcatcct    2580
tttacatggt tccatctac cctcacaaca catgtcatca ccaaagacac acatacaagc     2640
tccaatggct tttgccaggc aattcttcct ccaggacccc atctggcccc tcctcatcc     2700 ctcccttgg actttgccct tcttactggc caggcagggg ggccagagtc caggcttgac    2760
tcattcccac cttgtcctgg gctgagatcc caggtttgta acagaaaaca ccactaaagc    2820
cccagcacag gagagaacca cccagcccag aagttccagg gaaggaactc tccggtccac    2880
catggagtac ctctcagctc tgaacccag tgacttactc aggtgactgc taaccctccg     2940
ctctaccctc cacctttagg ggatataggc agggcaacaa tactccactc agcccctagg    3000
agactaacca gtaccccttc ctctcctgct ccccactcca cagtgggctt gtcaagctcc    3060
tgagccaccg gccccacct gcactccatg gtctctccct catccctaat cgataaacct     3120
agatctctcc ctccctagcc ctctagccac tctaccctca tcatgcccctt tacactcacc   3180 aagcccctcc tcgcccttc ttgactttc ttctcaacta ccaggtcagt atctaatata     3240
agctcggagt ttggacggag ggtctggacc tcagctccac caccccagcg accttccgt     3300
```

-continued

```
gtctgtgatc acaagcggac catccggaaa ggcctgacag ctgccacccg ccaggagctg    3360
ctagccaaag taagtaggcc aagttcctcg gttcctatag caggggtagc caaggggctc    3420
cacaacagtg gcaacttgtg atgatggagc agagggctga agtcacacag ctgcccctcc    3480
ctctgagggc taaaagcagc ggagtgggcc taatgagctc tggtcaattt gttcattttc    3540
cacctagtga gcttttctat gggagcaggg gttagcagga gatagggaga gttcgaggga    3600
cggaattcag aagctagtat ggaaaggtga tttgtgtgac aaatcaagtt caaattctga    3660
ttctgccact tcctgcctgt caaaccttgg aagttgttc aacctaccaa aacctcagtt     3720
tcttcaacta taaaaaggca ataataatac atcacctcct agggttgttg aaaggagtaa    3780
gaggataatg taggtaaagt cctcataacct ggcacagagt aaggactcaa aaaggttaaa   3840
cactattact gaaaacactt ctggagaact cttgagggtg tgggaagtga ggtgcagcat    3900
tgtagataag acagaagggt ggacttcatg agaacctggc ttgctttcca attccaaacc    3960
agaagtgact tggaggggag caaggggaga tgccaatgac atggtaggag caaagaggaa    4020 aaggtcagc ctctagctag gatcccccaa aaactgaaga acacggagag ctgcaacctt     4080
taggaggtat caaagtgcca gaaagtcaaa gtgggacatc gaccaatgtc tagagccaac    4140
tgatggatgt tgggcagcta agagggaag gggcatggga taagacctgc ccttcttgct     4200
tcttgccatt gggcaggcat tggagaccct actgctgaat ggagtgctaa ccctggtgct    4260
agaggaggat ggaactgcag tggacagtga ggacttcttc cagctgctgg aggatgacac    4320
gtgcctgatg gtgttgcagt ctggtcagag ctggagcccct acaagggtaa gaggcctata  4380
ctggggctgc ttccaatgcc tgtcctttag agctttcccg ggcttcctct ctagcttaac    4440
cctgatcctg ggaccaggt gcaggaggag ttgtggaatt gtcaaggatg tcacacagtg     4500
gacagaaagt ccaagcgagg gagggtctga cccagtgctg atggagatta gtggtgggtg    4560
tctggtatga ggatctactg cactgacaag ggtgtcctac agagtggagt gctgtcatat    4620
ggcctgggac gggagaggcc caagcacagc aaggacatcg cccgattcac ctttgacgtg    4680
tacaagcaaa accctcgaga cctctttggc agcctgaatg tcaaagccac attctacggg    4740
ctctactcta tgagttgtga ctttcaagga cttggcccaa agaaagtact caggtcagaa    4800
atcaacatgt catactgccc catccccatac agttggatag tccccataat tcgtcctctt    4860
gcacccacct acccctagtt agctcttgct tgtggaaagt cctcatctcc cagcttgatg    4920
gcttcctccc aagttttcca aatcatctga tttcctcttg tctctgccat tcagggagct    4980
ccttcgttgg acctccacac tgctgcaagg cctgggccat atgttgctgg gaatttcctc    5040
cacccttcgt catgcagtgg aggggctga gcagtggcag cagaagggcc gcctccattc     5100
ctactaaggg gctctgagct tctgccccca gaatcattcc aaccgaccca ctgcaaagac    5160
tatgacagca tcaaatttca ggacctgcag acagtacagg ctagataacc cacccaattt    5220
ccccactgtc ctctgatccc ctcgtgacag aacctttcag cataacgcct cacatcccaa    5280
gtctataccc ttacctgaag aatgctgttc tttcctagcc acctttctag cctcccactt    5340
gccctgaaag gccaagatca agatgtcccc caggcatctt gatcccagcc tgactgctgc    5400
tacatctaat cccctaccaa tgcctcctgt ccctaaactc cccagcatac tgatgacagc    5460
cctctctgac tttaccttga gatctgtctt catacccttc ccctcaaact aacaaaaaca    5520
tttccaataa aaatatcaaa tatttaccac taagacttct gactccaatt taaaccagga    5580
aagggatggg gtggataccc cattttgccc tcccccatca acacccagtc ccagatccaa    5640
agcctcagtc ttcaagtatg gagttcaatg cccgcctccg cttggccacc gcaccctgct    5700
```

-continued

```
gctgttccca agcctctcgc cgctttagga aggtagtcaa ggccacattt cgagccacat    5760
ggtggccgaa agggtctctt atcagctcct ggttctgctc ccctgcaaag gaaccactc    5820 atgtttagta ctaccatgct caaagacaga ctctacttga cgtaaagatc cctccatttc    5880
ccccagaccc tgggactgcc actgggataa agtgaacact tcactttcca agaacagaa    5940 gtcagagggc agggtgaggg cagaggacta cacaatcagt cagcgggagg gaaggggaaa    6000
gcagactgct aagaacccat gagcaagacc acccttggga actaaagact gttgaatttc    6060
agtagacttc ccagctaccc agtgatctgg agtaagagag gggagagtct ggaaacatca    6120
aagagagggg ctggtactca ccaagctcag cagcaatttc cttccgggcc ctcaaggctg    6180
ctccactcca gatggcatct agcacacggc tgccatggcg actacaggcc agagccacat    6240
attgtccctg tatggagaca agcaaagtag gtctccctag caaaatccac aaaagtattt    6300
tggaggcttg tggagagtga attttctgaa gagtttaagg gctgaattaa aatagtctag    6360
gaattacata gcctttttga gtctgaaggt acagtccagg gaaagctcat attctctaaa    6420
tggatgatgg tggggaatca aggcaaaagc cagaaatcta accttaggt tctgcagcac    6480 acggcggcgc acttgcgcgt cacagagggg ctggtcagga tggcatcgag cacatgagag    6540
ccagcgggac tttgggcaag ggacagaagc tgtggtcccg tcaaggcacc cagacttcga    6600
agtacaagac caggagtgga gaagtgcagc agatgctgga gcagtagaga cccaaggact    6660
gtcacatccc ccaaggctct ggctgcggcc attgccacct ggcagcgcag agataagaaa    6720
ttaggaggca ccaacaagcc aggtggatga gcccatcccc agaacactgc cacctccacc    6780
tggatgaagt caccactctc acctcagaag tcagacgctt gctaaaccct ggaggcctg    6840 actcccaatt agtcactggc ttggcctctc ccctacctca cctggtgctc tgcaggcact    6900 gcccctcct cctccgtcag tccatagtac acctcataag ccatcaaagt ggcaaagaga    6960
ggcacacagg ccacttgccg ggatgagggc tctgcacagt ggaatgccta aggagaaga    7020 caaaatatga tgaacctgag aacttctccg tcccttacct caactttaag ggaacacctt    7080
caggaaagga aagaaggccc aactccacaa gaatgatagc tcyatgaaag cagatgtcat    7140
gccttgctgt atccccagcc tctatcacat acagggggtta ataaatgttt atcccttaaa    7200
taaacttctc tcttagttct gggagacaat ttttgttcca ggactgtgaa ataacatttg    7260
gcctcagccg ggcacggtga gctgagattg cgccactgca ctccagcctg gcaacaaga    7320 gcaaaactcc gtctcaaaaa aaaaaaaaaa attagctggg tatggtggcg ggcacctata    7380
ggcctcattt tcccccattc ctgtgaactc cttgggcatt agacttcctg agtccagagg    7440
tacaaaaact taagattaga taagtcctaa aaggtagaag ttgaactgag ggcataaaca    7500
gattgtgggt aatatccact cacctccaac aagagctgta ggaccttggc ttggtaggcc    7560
ccaactctgc gacaggcccc caccagggca atgactaccc ctgggtggcc ctgggccaat    7620
acagcttcca agacagggct cagctcctca aacacagggg acagctgatg gaaacatgg    7680 aatgtaactc tggcattctg gtaatggcgg accacattat tcagagaaat cttcccaacg    7740
aaaacaacta aaaatgctag ataaaacata aaagcattg ccagtatcag gacttttgtt    7800
tggctagata aggcccagga taaggggca gtcttagagg tgccacctca caggaaggaa    7860
ctttaagtgg ctcttcccta tgtgtaaggg agcactagga gcaaggggag actaaaatta    7920
aactgcactt ccactctaac acccaatgca tgagaccaca gggaagccca ccttagtcct    7980
aagcagcaaa ggaaaagaga agctatggca acagctctag cactcatgtg ggcttatagc    8040
```

-continued

| | |
|---|---|
| caagtaccag agtctgggtg ggccatggaa cctcaagctg taaacctgaa taaagccagt | 8100 |
| ctcttgctgg tcctcatacc tgagagaagt caaaacaaat cctcactaga aggtgggcac | 8160 |
| ctttatccta agctctggaa aacctcaaag aatagctttt caagggcaat ggccagcaca | 8220 |
| atgtcaaagg tatatagagg cagacagacc ataaaataag gtccagtgat caagaattag | 8280 |
| cagaaacaga tccagctcag gtttccaact caccagctca ggggtagtga ctgcatccag | 8340 |
| taagcgctgc aaagggaagt tggcaatggg atgtgcagcc agggtctgca gctgcccctg | 8400 |
| caagtgctcc tcaaagaggc tctggagtct tgggggctcc aacaccagca ggacctgctc | 8460 |
| caggagtctg gaactcgtct gatctcggag aaatagcagt aggggactag ggacaagaag | 8520 |
| ggcatcaggc agtcttaact ccatttcatg caaaatacag ttgcactaca tcacctcatt | 8580 |
| catttcacac agccccgcca acttgggtcg atcctgaggc cctgaccata cctgccatct | 8640 |
| actgaggaac cgcgagtact caggtagcca atcacagcat tgcagaggtg agcgcaaaac | 8700 |
| tggggaagtt tgcggtgtaa aacctgtaaa gccacttgaa gacagaagct ggagatctta | 8760 |
| tcagtgataa acactgtgga gagagggcag aaataaagcg gctttctcaa aatccagaca | 8820 |
| acctgcgtaa cctcaaactt taggcaacaa gatacagggc actatggaca caaagggact | 8880 |
| atacaaagtg ctctgaacgt caaaccagac caggtttgaa aagaagagga ataacctgag | 8940 |
| gtaagggcct tgcttggtgg taagatgacc tccagacaag tagatacgag accatcctcc | 9000 |
| tacttccctc cttacctgca atgtccttca gaaaggagga gctcaggtcc tgaaggcgat | 9060 |
| tcaaaaaggt ttcagggact tcaaaatcag ctggcttaca ttcctgagct ggggtcttct | 9120 |
| gtgcttctga aggaagatta agaacatgtg cagtggggag atcacaaact gccatccagg | 9180 |
| agagaaaaat ttcacagatg aacaaggatt ccgcttggga atgcagaaca gatgtagtac | 9240 |
| aactaaatgt ctcttctgga tgactgaact gagactacat ttctgtctta attttttctaa | 9300 |
| gaaacttcaa ccagcttccc catggtccac agaagacagt tcaacctcct cagccaggta | 9360 |
| ttcaagccat tccaaaataa agcctcattt aaactcgcta actttatttc ctagtttttc | 9420 |
| aaaatgtgga tcacagctca agactgtacc atgaaatcaa gttagtggtc tcaactagca | 9480 |
| ttttttttaa atgaaataga gcagaatagt tttgaaaagg aaaaaaaaat aacagagtgg | 9540 |
| gctgcatgta gtaagggtat agtttcctga actyttgctt gagtccagtg tgtatgttac | 9600 |
| ttttgcttaa gtccatttgt atattaagtc atgcttaaaa aaaattctcc tcctgcgtcc | 9660 |
| attctaatag cctcccccaa acacaactgt acatccctac ctctgggcct ccgcacacac | 9720 |
| taatctttgg cttgctaagc cctgttcaga ttaggacagg tcaagctaat tcttcccggt | 9780 |
| caagctcccc catgaagact tactcttctg tttactgtct cattctgaac tttctaaatt | 9840 |
| cttcttcccc ctaggtccac tttcctcttg taatacttac cagatgattg ggaaccacgg | 9900 |
| ggcctggctc tctcagactc cagaatagtc cctcctaaca cctgaagcag agttctgacc | 9960 |
| acgaagctgc catgtgtgtc tccacagtag acaagaaaat catcacacac ctcagcggct | 10020 |
| agtcccagga ccagctcctc cagggtctcc gtgggaccat cctttccatc ctcctcctcc | 10080 |
| tcctcctcct cctcctctgc agcactcccc agcaatcgag ggagctgtag caaagcactt | 10140 |
| tgtaatacat ggaccccgca tcggtgacag gccacagtgc gcaagttaga gcgcagagca | 10200 |
| gcccacacgc gacaaagcgg tttcaaggga ctgaatccca acagttcctg cagcatctca | 10260 |
| ctgccagtcc tgttcgtgga caaagctagg gcctgagtct ctacttcctt cattatattg | 10320 |
| tgcaccatca gatctgaaaa gggaagaaag acacactttg aagagactta gtagagaata | 10380 |
| cagttatgta ccctcgctta accaagggtc gtgggtcgga ggccgaggaa gaggacatgg | 10440 |

-continued

```
gaaatgaaac taagtcccca cgccctgccg accctagaaa gtttccttgc ctgccctgga    10500
tttgatgctc ttggtctaaa ccccgaagtt gctgcctacc tcgttcttcc ccagtctcgg    10560
gagcctcttt caatgctgac agcgcccggc ggaaatatcc cagagcttcc gggctcaggt    10620
gcgggtgcga atctggagcc ggctccgagc gcccatccgg aggcggccag ggttgccgct    10680
tacggcctgg taagggcgc cccgacccct tggccccgcg ccccgtttg ccaccagctg     10740 ggaaccggcg ccccaccttg tgtggagagc gcggaccctg cccatgtgt gcttcgcgac     10800 ctgtccggct gcaaaagctt ccttaactgc ggacggacct tcgacgtcgc caagcgtgcg    10860
ccttatccag acaaagttta gaaacgcggg cgcgctcctg acgcagctac tacgtcatag    10920
ttccgcgccg cccagccgg gcggggtggg tgtgtcaccc a                         10961
```

<210> SEQ ID NO 2
<211> LENGTH: 1187
<212> TYPE: DNA
<213> ORGANISM: Homo sapiens
<220> FEATURE:
<221> NAME/KEY: 5'UTR
<222> LOCATION: 1..79
<221> NAME/KEY: CDS
<222> LOCATION: 80..739
<221> NAME/KEY: 3'UTR
<222> LOCATION: 740..1187
<221> NAME/KEY: polyA_signal
<222> LOCATION: 1158..1163
<223> OTHER INFORMATION: AATAAA
<221> NAME/KEY: misc_feature
<222> LOCATION: 1..241
<223> OTHER INFORMATION: homology with 5' EST in ref : Genset 93-5-2-G3-PU

<400> SEQUENCE: 2

```
agaaaacacc actaaagccc cagcacagga gagaaccacc cagcccagaa gttccaggga     60
aggaactctc cggtccacc atg gag tac ctc tca gct ctg aac ccc agt gac    112
                    Met Glu Tyr Leu Ser Ala Leu Asn Pro Ser Asp
                     1               5                  10 tta ctc agg tca gta tct aat ata agc tcg gag ttt gga cgg agg gtc    160
Leu Leu Arg Ser Val Ser Asn Ile Ser Ser Glu Phe Gly Arg Arg Val
            15                  20                  25 tgg acc tca gct cca cca ccc cag cga cct ttc cgt gtc tgt gat cac    208
Trp Thr Ser Ala Pro Pro Pro Gln Arg Pro Phe Arg Val Cys Asp His
        30                  35                  40 aag cgg acc atc cgg aaa ggc ctg aca gct gcc acc cgc cag gag ctg    256
Lys Arg Thr Ile Arg Lys Gly Leu Thr Ala Ala Thr Arg Gln Glu Leu
    45                  50                  55 cta gcc aaa gca ttg gag acc cta ctg ctg aat gga gtg cta acc ctg    304
Leu Ala Lys Ala Leu Glu Thr Leu Leu Leu Asn Gly Val Leu Thr Leu
60                  65                  70                  75 gtg cta gag gag gat gga act gca gtg gac agt gag gac ttc ttc cag    352
Val Leu Glu Glu Asp Gly Thr Ala Val Asp Ser Glu Asp Phe Phe Gln
                80                  85                  90 ctg ctg gag gat gac acg tgc ctg atg gtg ttg cag tct ggt cag agc    400
Leu Leu Glu Asp Asp Thr Cys Leu Met Val Leu Gln Ser Gly Gln Ser
            95                  100                 105 tgg agc cct aca agg agt gga gtg ctg tca tat ggc ctg gga cgg gag    448
Trp Ser Pro Thr Arg Ser Gly Val Leu Ser Tyr Gly Leu Gly Arg Glu
        110                 115                 120 agg ccc aag cac agc aag gac atc gcc cga ttc acc ttt gac gtg tac    496
Arg Pro Lys His Ser Lys Asp Ile Ala Arg Phe Thr Phe Asp Val Tyr
    125                 130                 135
```

-continued

```
aag caa aac cct cga gac ctc ttt ggc agc ctg aat gtc aaa gcc aca    544
Lys Gln Asn Pro Arg Asp Leu Phe Gly Ser Leu Asn Val Lys Ala Thr
140                 145                 150                 155 ttc tac ggg ctc tac tct atg agt tgt gac ttt caa gga ctt ggc cca    592
Phe Tyr Gly Leu Tyr Ser Met Ser Cys Asp Phe Gln Gly Leu Gly Pro
                160                 165                 170 aag aaa gta ctc agg gag ctc ctt cgt tgg acc tcc aca ctg ctg caa    640
Lys Lys Val Leu Arg Glu Leu Leu Arg Trp Thr Ser Thr Leu Leu Gln
            175                 180                 185 ggc ctg ggc cat atg ttg ctg gga att tcc tcc acc ctt cgt cat gca    688
Gly Leu Gly His Met Leu Leu Gly Ile Ser Ser Thr Leu Arg His Ala
        190                 195                 200 gtg gag ggg gct gag cag tgg cag cag aag ggc cgc ctc cat tcc tac    736
Val Glu Gly Ala Glu Gln Trp Gln Gln Lys Gly Arg Leu His Ser Tyr
    205                 210                 215 taa gggctctga gcttctgccc ccagaatcat tccaaccgac ccactgcaaa          789
  *
220 gactatgaca gcatcaaatt tcaggacctg cagacagtac aggctagata acccacccaa    849 tttccccact gtcctctgat cccctcgtga cagaaccttt cagcataacg cctcacatcc    909 caagtctata cccttacctg aagaatgctt ttctttccta gccacctttc tagcctccca    969 cttgccctga aaggccaaga tcaagatgtc ccccaggcat cttgatccca gcctgactgc   1029 tgctacatct aatccctac caatgcctcc tgtccctaaa ctccccagca tactgatgac   1089 agccctctct gactttacct tgagatctgt cttcatacc ttcccctcaa actaacaaaa   1149 acatttccaa taaaaatatc aaatatttac cactaaga                          1187
```

<210> SEQ ID NO 3
<211> LENGTH: 219
<212> TYPE: PRT
<213> ORGANISM: Homo sapiens

<400> SEQUENCE: 3

```
Met Glu Tyr Leu Ser Ala Leu Asn Pro Ser Asp Leu Leu Arg Ser Val
1               5                   10                  15

Ser Asn Ile Ser Ser Glu Phe Gly Arg Arg Val Trp Thr Ser Ala Pro
            20                  25                  30

Pro Pro Gln Arg Pro Phe Arg Val Cys Asp His Lys Arg Thr Ile Arg
        35                  40                  45

Lys Gly Leu Thr Ala Ala Thr Arg Gln Glu Leu Ala Lys Ala Leu
    50                  55                  60

Glu Thr Leu Leu Leu Asn Gly Val Leu Thr Leu Val Leu Glu Glu Asp
65                  70                  75                  80

Gly Thr Ala Val Asp Ser Glu Asp Phe Phe Gln Leu Leu Glu Asp Asp
                85                  90                  95

Thr Cys Leu Met Val Leu Gln Ser Gly Gln Ser Trp Ser Pro Thr Arg
            100                 105                 110

Ser Gly Val Leu Ser Tyr Gly Leu Gly Arg Glu Arg Pro Lys His Ser
        115                 120                 125

Lys Asp Ile Ala Arg Phe Thr Phe Asp Val Tyr Lys Gln Asn Pro Arg
    130                 135                 140

Asp Leu Phe Gly Ser Leu Asn Val Lys Ala Thr Phe Tyr Gly Leu Tyr
145                 150                 155                 160

Ser Met Ser Cys Asp Phe Gln Gly Leu Gly Pro Lys Lys Val Leu Arg
                165                 170                 175
```

```
Glu Leu Leu Arg Trp Thr Ser Thr Leu Leu Gln Gly Leu Gly His Met
            180                 185                 190

Leu Leu Gly Ile Ser Ser Thr Leu Arg His Ala Val Glu Gly Ala Glu
        195                 200                 205

Gln Trp Gln Gln Lys Gly Arg Leu His Ser Tyr
    210                 215

<210> SEQ ID NO 4
<211> LENGTH: 18
<212> TYPE: DNA
<213> ORGANISM: Artificial Sequence
<220> FEATURE:
<223> OTHER INFORMATION: sequencing oligonucleotide PrimerPU

<400> SEQUENCE: 4
tgtaaaacga cggccagt                                                         18

<210> SEQ ID NO 5
<211> LENGTH: 18
<212> TYPE: DNA
<213> ORGANISM: Artificial Sequence
<220> FEATURE:
<223> OTHER INFORMATION: sequencing oligonucleotide PrimerRP

<400> SEQUENCE: 5
caggaaacag ctatgacc                                                         18
```

US 6,472,517 B1

NUCLEIC ACIDS ENCODING HUMAN CIDE-B PROTEIN AND POLYMORPHIC MARKERS THEREOF

The application is the National Stage of International Application PCT/IB99/01702, filed Oct. 8, 1999, which claims the benefit of U.S. Provisional Application No. 60/103,729, filed Oct. 9, 1998.

FIELD OF THE INVENTION

The present invention relates to a purified or isolated polynucleotide encoding human CIDE B protein, the regulatory nucleic acids contained therein, polymorphic markers thereof, and the resulting encoded protein, as well as to methods and kits for detecting this polynucleotide and this protein. The present invention also pertains to a polynucleotide carrying the natural regulatory regions of the CIDE B gene which is useful, for example, to express a heterologous nucleic acid in host cells or host organisms as well as functionally active regulatory polynucleotides derived from said regulatory regions.

BACKGROUND OF THE INVENTION

Apoptosis is of fundamental importance to biological processes including embryogenesis, maintenance of tissue homeostasis, normal cellular development of multicellular organisms, elimination of virus-infected cells, and the development of immune system. It is a type of death that is fundamentally distinct from degenerative death or necrosis in that it is an active process of gene-directed cellular self-destruction which, in some instances serves a biologically meaningful homeostatic function. Necrosis, in contrast, is cell death occurring as a result of severe injurious changes in the environment of infected cells.

Morphologically, apoptosis is characterized by the rapid condensation of the cell with preservation of membranes. Synchronistically with the compaction of chromatin, several biochemical changes occur in the cell. Nuclear DNA is cleaved at the linker regions between nucleosomes to produce fragments that are easily demonstrated by agarose gel electrophoresis wherein a characteristic ladder develops.

The primary image of apoptosis is that of the dying thymocyte: fusion of chromatin into one mass, which binds to the nuclear membrane, while the cytoplasm remains apparently intact before beginning to condense. The nuclear change is one of the earliest visible processes; the conversion to the condensed state occurs rapidly and is accompanied by endonucleolytic degradation of DNA between nucleosomes. Once the chromatin has condensed, electrophoresis of the DNA demonstrates a ladder of fragments differing in size by 180 bp, generated by an enzymatic activity resembling that of DNase I.

This type of cell death is seen in many varieties of cells, especially those that, like lymphocytes or thymocytes, have relatively little cytoplasm and are highly mitotic or derive from highly mitotic lines. In this situation, in which mitotic cells are likely to face challenges by mutagens (viruses, toxins), an appropriate biological imperative would be to destroy the DNA rapidly and effectively. Thus, this type of cell death is particularly dramatic among hematopoietic cells and their derivatives.

Several regulatory components of the apoptotic pathway have been identified in various living organisms including man and the nematode *Caenorhabditis elegans*.

Two murine transcription products involved in cell apoptosis have been reported by Inohara et al. (1998), that have been named respectively CIDE-A and CIDE-B. Murine CIDE-A and CIDE-B have strong homology with the murine anti-apoptosis DFF45 protein as well as with the drosophila protein DREP-1. The homology of CIDE-A, CIDE-B and FSP27 with DFF45 was restricted to an N-terminal region designated by Inohara et al. as CIDE-N domain which showed 39, 29 and 38% amino acid identity respectively with DFF45.

Because there is a strong need in the art to make available to the public novel means useful to prevent or inhibit apoptosis disorders, either in the case of disorders caused by abnormal cell proliferation wherein apoptosis induction is desirable or in the case of disorders caused by abnormal cell death wherein an inhibition or an arrest of apoptosis is desirable, the inventors have attempted to isolate and characterize a novel gene encoding a protein involved in apoptosis pathway, namely the human CIDE-B gene.

SUMMARY OF THE INVENTION

The present invention pertains to a nucleic acid molecule comprising the genomic sequence of the human CIDE B gene. The CIDE B genomic sequence comprises regulatory sequences located both upstream (5'-end) and downstream (3'-end) of the transcribed portion of said gene, these regulatory sequences being also part of the invention.

The invention also deals with the complete cDNA sequence encoding the CIDE B protein, as well as with the corresponding translation product.

Oligonucleotide probes or primers hybridizing specifically with a CIDE B genomic or cDNA sequence are also part of the present invention.

A further object of the invention consists of recombinant vectors comprising any of the nucleic acid sequences above described, and in particular of recombinant vectors comprising a CIDE B regulatory sequence or a sequence encoding a CIDE B protein, as well as of cell hosts comprising said nucleic acid sequences or recombinant vectors.

Finally, the invention is directed to methods for the screening of substances or molecules which modulate the expression of CIDE B.

The invention is also directed to biallelic markers that are located within the CIDE B genomic sequence, these biallelic markers representing useful tools in order to identify a statistically significant association between specific alleles of CIDE B gene and one or several disorders related to apoptosis such as cancer and AIDS.

BRIEF DESCRIPTION OF THE SEQUENCES PROVIDED IN THE SEQUENCE LISTING

Figure 1:
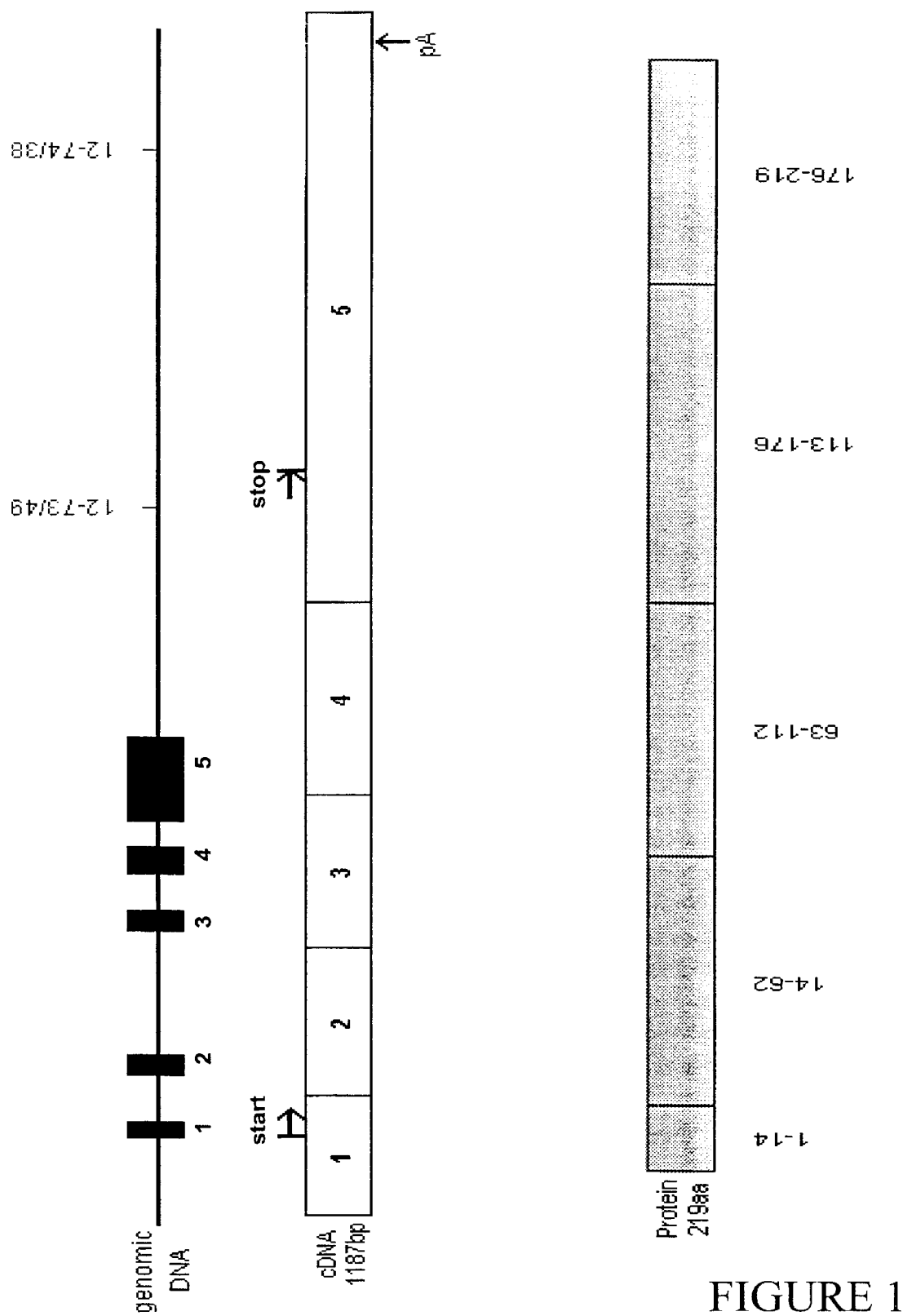
FIG. 1 is a diagram of the CIDE B1 gene with an indication of the relative position of the biallelic markers of the present invention. The upper line refers to the genomic sequence of CIDE B. The middle line refers to the cDNA. The lower line refers to the CIDE B protein.

SEQ ID No 1 contains a genomic sequence of CIDE B comprising the 5' regulatory region (upstream untranscribed region), the exons and introns, and the 3' regulatory region (downstream untranscribed region).

SEQ ID No 2 contains a cDNA sequence of CIDE B.

SEQ ID No 3 contains the amino acid sequence encoded by the cDNA of SEQ ID No 2.

SEQ ID No 4 contains a primer containing the additional PU 5' sequence described further in Example 2

SEQ ID No 5 contains a primer containing the additional RP 5' sequence described further in Example 2.

In accordance with the regulations relating to Sequence Listings, the following codes have been used in the Sequence Listing to indicate the locations of biallelic markers within the sequences and to identify each of the alleles present at the polymorphic base. The code "r" in the sequences indicates that one allele of the polymorphic base is a guanine, while the other allele is an adenine. The code "y" in the sequences indicates that one allele of the polymorphic base is a thymine, while the other allele is a cytosine. The code "m" in the sequences indicates that one allele of the polymorphic base is an adenine, while the other allele is an cytosine. The code "k" in the sequences indicates that one allele of the polymorphic base is a guanine, while the other allele is a thymine. The code "s" in the sequences indicates that one allele of the polymorphic base is a guanine, while the other allele is a cytosine. The code "w" in the sequences indicates that one allele of the polymorphic base is an adenine, while the other allele is an thymine. The nucleotide code of the original allele for each biallelic marker is the following:

| Biallelic marker | Original allele |
| --- | --- |
| 12-73-49 | C |
| 12-74-38 | T |

DETAILED DESCRIPTION OF THE INVENTION

The aim of the present invention is to provide the human CIDE B gene, the human CIDE B mRNA molecules and the polynucleotides derived from them. The polynucleotides of the invention are useful to design suitable means for detecting the presence of this gene or cDNA in a test sample and to design suitable means to express a desired polynucleotide of interest. The invention also relates to the human CIDE B polypeptide.

Definitions

Before describing the invention in greater detail, the following definitions are set forth to illustrate and define the meaning and scope of the terms used to describe the invention herein.

The terms "CIDE B gene", when used herein, encompasses genomic, mRNA and cDNA sequences encoding the CIDE B protein.

The term "heterologous protein", when used herein, is intended to designate any protein or polypeptide other than the CIDE B protein. More particularly, the heterologous protein is a compound which can be used as a marker in further experiments with a CIDE B regulatory region.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "purified" does not require absolute purity; rather, it is intended as a relative definition. Purification of starting material or natural material to at least one order of magnitude, preferably two or three orders, and more preferably four or five orders of magnitude is expressly contemplated. As an example, purification from 0.1% concentration to 10% concentration is two orders of magnitude. The term "purified" is used herein to describe a polynucleotide or polynucleotide vector of the invention which has been separated from other compounds including, but not limited to other nucleic acids, carbohydrates, lipids and proteins (such as the enzymes used in the synthesis of the polynucleotide), or the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polynucleotide typically comprises about 50%, preferably 60 to 90% weight/weight of a nucleic acid sample, more usually about 95%, and preferably is over about 99% pure. Polynucleotide purity or homogeneity is indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

The term "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

The term "purified" is used herein to describe a polypeptide of the invention which has been separated from other compounds including, but not limited to nucleic acids, lipids, carbohydrates and other proteins. A polypeptide is substantially pure when at least about 50%, preferably 60 to 75% of a sample exhibits a single polypeptide sequence. A substantially pure polypeptide typically comprises about 50%, preferably 60 to 90% weight/weight of a protein sample, more usually about 95%, and preferably is over about 99% pure. Polypeptide purity or homogeneity is indicated by a number of means well known in the art, such as polyacrylamide gel electrophoresis of a sample, followed by visualizing a single polypeptide band upon staining the gel. For certain purposes higher resolution can be provided by using HPLC or other means well known in the art.

As used herein, the term "non-human animal" refers to any non-human vertebrate, birds and more usually mammals, preferably primates, farm animals such as swine, goats, sheep, donkeys, and horses, rabbits or rodents, more preferably rats or mice. As used herein, the term "animal" is used to refer to any vertebrate, preferable a mammal. Both the terms "animal" and "mammal" expressly embrace human subjects unless preceded with the term "non-human".

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments.

As used herein, an "antigenic determinant" is the portion of an antigen molecule, in this case a CIDE B polypeptide, that determines the specificity of the antigen-antibody reaction. An "epitope" refers to an antigenic determinant of a polypeptide. An epitope can comprise as few as 3 amino acids in a spatial conformation which is unique to the epitope. Generally an epitope comprises at least 6 such amino acids, and more usually at least 8–10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

Throughout the present specification, the expression "nucleotide sequence" may be employed to designate indifferently a polynucleotide or a nucleic acid. More precisely, the expression "nucleotide sequence" encompasses the nucleic material itself and is thus not restricted to the sequence information (i.e. the succession of letters chosen among the four base letters) that biochemically characterizes a specific DNA or RNA molecule.

As used interchangeably herein, the terms "nucleic acids", "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

A "promoter" refers to a DNA sequence recognized by the synthetic machinery of the cell required to initiate the specific transcription of a gene.

A sequence which is "operably linked" to a regulatory sequence such as a promoter means that said regulatory element is in the correct location and orientation in relation to the nucleic acid to control RNA polymerase initiation and expression of the nucleic acid of interest.

As used herein, the term "operably linked" refers to a linkage of polynucleotide elements in a functional relationship. For instance, a promoter or enhancer is operably linked to a coding sequence if it affects the transcription of the coding sequence. More precisely, two DNA molecules (such as a polynucleotide containing a promoter region and a polynucleotide encoding a desired polypeptide or polynucleotide) are said to be "operably linked" if the nature of the linkage between the two polynucleotides does not (1) result in the introduction of a frame-shift mutation or (2) interfere with the ability of the polynucleotide containing the promoter to direct the transcription of the coding polynucleotide.

The term "primer" denotes a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase.

The term "probe" denotes a defined nucleic acid segment (or nucleotide analog segment, e.g., polynucleotide as defined hereinbelow) which can be used to identify a specific polynucleotide sequence present in samples, said nucleic acid segment comprising a nucleotide sequence complementary of the specific polynucleotide sequence to be identified.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, without to be limited to, cancers, developmental diseases, and neurological diseases.

The term "allele" is used herein to refer to variants of a nucleotide sequence. A biallelic polymorphism has two forms. Diploid organisms may be homozygous or heterozygous for an allelic form.

The term "genotype" as used herein refers the identity of the alleles present in an individual or a sample. In the context of the present invention, a genotype preferably refers to the description of the biallelic marker alleles present in an individual or a sample. The term "genotyping" a sample or an individual for a biallelic marker involves determining the specific allele or the specific nucleotide carried by an individual at a biallelic marker.

The term "mutation" as used herein refers to a difference in DNA sequence between or among different genomes or individuals which has a frequency below 1%.

The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. In the context of the present invention, "single nucleotide polymorphism" preferably refers to a single nucleotide substitution. Typically, between different individuals, the polymorphic site may be occupied by two different nucleotides.

The term "biallelic polymorphism" and "biallelic marker" are used interchangeably herein to refer to a single nucleotide polymorphism having two alleles at a fairly high frequency in the population. A "biallelic marker allele" refers to the nucleotide variants present at a biallelic marker site.

The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center", and so on.

Biallelic markers can be defined as genome-derived polynucleotides having between 2 and 100, preferably between 20, 30, or 40 and 60, and more preferably about 47 nucleotides in length, which exhibit biallelic polymorphism at one single base position. Each biallelic marker therefore corresponds to two forms of a polynucleotide sequence included in a gene which, when compared with one another, present a nucleotide modification at one position.

The term "upstream" is used herein to refer to a location which is toward the 5' end of the polynucleotide from a specific reference point.

The terms "base paired" and "Watson & Crick base paired" are used interchangeably herein to refer to nucleotides which can be hydrogen bonded to one another be virtue of their sequence identities in a manner like that found in double-helical DNA with thymine or uracil residues linked to adenine residues by two hydrogen bonds and cytosine and guanine residues linked by three hydrogen bonds (See Stryer, 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

Variants and Fragments

1-Polynucleotides

The invention also relates to variants and fragments of the polynucleotides described herein.

Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Nucleotide changes present in a variant polynucleotide may be silent, which means that they do not alter the amino acids encoded by the polynucleotide.

However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions.

In the context of the present invention, particularly preferred embodiments are those in which the polynucleotides encode polypeptides which retain substantially the same biological function or activity as the mature CIDE B protein.

Variants of polynucleotides according to the invention include, without being limited to, nucleotide sequences at least 95% identical to a nucleic acid selected from the group consisting of SEQ ID Nos 1 and 2, and any polynucleotide fragment of at least 8, 20, 50, 75, or 100 consecutive nucleotides from a nucleic acid selected from the group consisting of SEQ ID Nos 1 and 2, and preferably at least 99% identical, more particularly at least 99.5% identical, and most preferably at least 99.8% identical to a nucleic acid selected from the group consisting of SEQ ID Nos 1 and 2, and any polynucleotide fragment of at least 8, 20, 50, 75, or 100 consecutive nucleotides from a nucleic acid selected from the group consisting of SEQ ID Nos 1 and 2.

A polynucleotide fragment is a polynucleotide having a sequence that is entirely the same as part but not all of a given nucleotide sequence, preferably the nucleotide sequence of a CIDE B gene, and variants thereof. The fragment can be a portion of an exon or of an intron of a CIDE B gene. It can also be a portion of the regulatory sequences of the CIDE B gene, preferably of the promoter. Preferably, such fragments comprise at least one of the biallelic markers 12-73-49 and 12-74-38 or a biallelic marker in linkage disequilibrium therewith.

Such fragments may be "free-standing", i.e. not part of or fused to other polynucleotides, or they may be comprised within a single larger polynucleotide of which they form a part or region. However, several fragments may be comprised within a single larger polynucleotide.

As representative examples of polynucleotide fragments of the invention, there may be mentioned those which have from about 4, 6, 8, 15, 20, 25, 40, 10 to 30, 30 to 55, 50 to 100, 75 to 100 or 100 to 200 nucleotides in length. Preferred are those fragments having about 47 nucleotides in length, such as those comprising one of the biallelic markers 12-73-49 and 12-74-38. Preferred polynucleotide fragments according to the invention comprise a contiguous span of at least 35, 40, 50, 60, 70, 80, 90, 100, 150, 200, 500, or 1000 nucleotides of one particular nucleic acid.

2-Polypeptides

The invention also relates to variants, fragments, analogs and derivatives of the polypeptides described herein, including mutated CIDE B proteins.

The variant may be 1) one in which one or more of the amino acid residues are substituted with a conserved or non-conserved amino acid residue and such substituted amino acid residue may or may not be one encoded by the genetic code, or 2) one in which one or more of the amino acid residues includes a substituent group, or 3) one in which the mutated CIDE B is fused with another compound, such as a compound to increase the half-life of the polypeptide (for example, polyethylene glycol), or 4) one in which the additional amino acids are fused to the mutated CIDE B, such as a leader or secretory sequence or a sequence which is employed for purification of the mutated CIDE B or a preprotein sequence. Such variants are deemed to be within the scope of those skilled in the art.

More particularly, a variant CIDE B polypeptide comprises amino acid changes ranging from 1, 2, 3, 4, 5, 10 to 20 substitutions, additions or deletions of one aminoacid, preferably from 1 to 10, more preferably from 1 to 5 and most preferably from 1 to 3 substitutions, additions or deletions of one amino acid. The preferred amino acid changes are those which have little or no influence on the biological activity or the capacity of the variant CIDE B polypeptide to be recognized by antibodies raised against a native CIDE B protein.

By homologous peptide according to the present invention is meant a polypeptide containing one or several aminoacid additions, deletions and/or substitutions in the amino acid sequence of a CIDE B polypeptide. In the case of an aminoacid substitution, one or several-consecutive or non-consecutive-aminoacids are replaced by <<equivalent>> aminoacids.

In the case of an amino acid substitution in the amino acid sequence of a polypeptide according to the invention, one or several amino acids can be replaced by "equivalent" amino acids. The expression "equivalent" amino acid is used herein to designate any amino acid that may be substituted for one of the amino acids having similar properties, such that one skilled in the art of peptide chemistry would expect the secondary structure and hydropathic nature of the polypeptide to be substantially unchanged. Generally, the following groups of amino acids represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

A specific embodiment of a modified CIDE B peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2—O) methylene-oxy bond, a (CH2—S) thiomethylene bond, a (CH2CH2) carba bond, a (CO—CH2) cetomethylene bond, a (CHOH—CH2) hydroxyethylene bond), a (N—N) bound, a E-alcene bond or also a —CH=CH— bond. The invention also encompasses a human CIDE B polypeptide or a fragment or a variant thereof in which at least one peptide bond has been modified as described above.

The polypeptide according to the invention could have post-translational modifications. For example, it can present the following modifications: acylation, disulfide bond formation, prenylation, carboxymethylation and phosphorylation.

A polypeptide fragment is a polypeptide having a sequence that entirely is the same as part but not all of a given polypeptide sequence, preferably a polypeptide encoded by a CIDE B gene and variants thereof.

Such fragments may be "free-standing", i.e. not part of or fused to other polypeptides, or they may be comprised within a single larger polypeptide of which they form a part or region. However, several fragments may be comprised within a single larger polypeptide.

As representative examples of polypeptide fragments of the invention, there may be mentioned those which have from about 5, 6, 7, 8, 9 or 10 to 15, 10 to 20, 15 to 40, or 30 to 55 amino acids long. Preferred polypeptide fragments according to the invention comprise a contiguous span of at least 8 amino acids, preferably at least 10 amino acids, more preferably at least 12, 15, 20, 25, 30, 40, 50, 100, 150 or 200 amino acids of one amino acid sequence. Preferred are those fragments containing at least one amino acid mutation in the CIDE B protein.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST") which is well known in the art (see, e.g., Karlin and Altschul, 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., 1992; Henikoff and Henikoff, 1993). Less preferably, the PAM or PAM250 matrices may also be used (see, e.g., Schwartz and Dayhoff, eds., 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990).

The BLAST programs may be used with the default parameters or with modified parameters provided by the user.

Stringent Hybridization Conditions

By way of example and not limitation, procedures using conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in prehybridization mixture containing 100 µg/ml denatured salmon sperm DNA and 5–20× $10^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and cited in Sambrook et al., 1989; and Ausubel et al., 1989. These hybridization conditions are suitable for a nucleic acid molecule of about 20 nucleotides in length. There is no need to say that the hybridization conditions described above are to be adapted according to the length of the desired nucleic acid, following techniques well known to the one skilled in the art. The suitable hybridization conditions may for example be adapted according to the teachings disclosed in the book of Hames and Higgins (1985) or in Sambrook et al.(1989).

Genomic Sequences of CIDE B

The present invention comprises a purified or isolated nucleic acid encoding the CIDE B polypeptide, wherein said nucleic acid comprising the sequence of SEQ ID No 1, a sequence complementary thereto, a fragment or a variant thereof.

The invention also encompasses a purified or isolated nucleic acid comprising a nucleotide sequence having at least 70, 75, 80, 85, 90, or 95% nucleotide identity with the nucleotide sequence of SEQ ID No 1, a sequence complementary thereto, or a fragment thereof. The nucleotide differences as regards to the nucleotide sequences of SEQ ID No 1 are generally randomly distributed throughout the entire nucleic acid. Nevertheless, preferred nucleic acids are those wherein the nucleotide differences as regards to the nucleotide sequences of SEQ ID No 1 are predominantly located outside the coding sequences contained in the exons.

Another object of the invention consists of a purified, isolated, or recombinant nucleic acid that hybridizes with the sequence of SEQ ID No 1 or a complementary sequence thereto or a variant thereof, under the stringent hybridization conditions as defined above.

These nucleic acids, as well as their fragments and variants, may be used as oligonucleotide primers or probes in order to detect the presence of a copy of the CIDE B gene in a test sample, or alternatively in order to amplify a target nucleotide sequence within the CIDE B sequences.

The CIDE B gene has 5 exons. The exon and intron positions in SEQ ID No 1 are detailed below in Table A.

TABLE A

| | Position in SEQ ID No 1 | | | Position in SEQ ID No 1 | |
|---|---|---|---|---|---|
| Exon | Beginning | End | Intron | Beginning | End |
| 1 | 2803 | 2922 | 1 | 2923 | 3224 |
| 2 | 3225 | 3369 | 2 | 3370 | 4216 |
| 3 | 4717 | 4366 | 3 | 4367 | 4602 |
| 4 | 4603 | 4793 | 4 | 4794 | 4974 |
| 5 | 4975 | 5555 | | | |

Consequently, the invention also concerns a purified or isolated nucleic acid comprising a nucleotide sequence selected from the group consisting of the exons 1, 2, 3, 4, and 5 of the CIDE B gene, a sequence complementary thereto, a fragment or a variant thereof.

The invention also deals with a purified or isolated nucleic acid comprising a combination of at least two polynucleotides selected from the group consisting of the exons 1, 2, 3, 4, and 5 of the CIDE B gene, wherein the polynucleotides are ordered within the nucleic acid, from the 5' end to the 3' end of said nucleic acid, in the same order than in the SEQ ID No 1.

Thus, the invention embodies purified, isolated, or recombinant polynucleotides comprising a nucleotide sequence selected from the group consisting of the introns of the CIDE B gene, or a sequence complementary thereto.

Particularly preferred nucleic acids of the invention include isolated, purified, or recombinant polynucleotides comprising a contiguous span of at least 35, 40, 50, 60, 70, 80, 90, 100, 150, 200, 500, or 1000 nucleotides of the nucleotide sequence of SEQ ID No 1, or the complements thereof. Additionally preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1–1000, 1001–2000, 2001–3000, 3001–4000, 4001–5000, 5001–6000, 6001–7000, 7001–8000, 8001–9000, 9001–10000, 10001–10961.

While this section is entitled "Genomic Sequences of CIDE B," it should be noted that nucleic acid fragments of any size and sequence may also be comprised by the polynucleotides described in this section, flanking the genomic sequences of CIDE B on either side or between two or more such genomic sequences.

CIDE B cDNA Sequences

The inventors have discovered that the expression of the CIDE B gene leads to the production of at least one mRNA molecule, the nucleic acid sequence of which is set forth in SEQ ID No 2.

Another object of the invention consists of a purified or isolated nucleic acid comprising the nucleotide sequence of SEQ ID No 2 or fragments or variants thereof, or a complementary sequence thereto.

The invention also pertains to a purified or isolated nucleic acid having at least 70, 75, 80, 85, 90, or 95% nucleotide identity with the nucleotide sequence of SEQ ID No 2, a sequence complementary thereto, or a fragment thereof.

Another object of the invention consists of a purified, isolated, or recombinant nucleic acid that hybridizes with the sequence of SEQ ID No 2 or a complementary sequence thereto or a variant thereof, under the stringent hybridization conditions as defined above.

The nucleotide differences as regards to the nucleotide sequence of SEQ ID No 2 are generally randomly distributed throughout the entire nucleic acid. Nevertheless, preferred nucleic acids are those wherein the nucleotide differences as regards to the nucleotide sequence of SEQ ID No 2 are predominantly located outside the coding sequences, and more precisely in the 5'-UTR and the 3'-UTR sequences contained in the nucleotide sequence of SEQ ID No 2.

The cDNA of SEQ ID No 2 includes a 5'-UTR region starting from the nucleotide at position 1 and ending at the nucleotide in position 79 of SEQ ID No 2. The cDNA of SEQ ID No 2 includes a 3'-UTR region starting from the nucleotide at position 740 and ending at the nucleotide at position 1187 of SEQ ID No 2.

Consequently, the invention concerns a purified or isolated nucleic acid comprising a nucleotide sequence selected from a group consisting of the 5'UTR and 3'UTR of the CIDE B cDNA, a sequence complementary thereto, a fragment or a variant thereof.

The middle line of FIG. 1 depicts the main structural features of a purified or isolated nucleic acid consisting of a CIDE B cDNA. The 5'-end sequence of this cDNA, more particularly the nucleotide sequence comprised between the nucleotide in position 1 and the nucleotide in position 247 of the nucleic acid of SEQ ID No 2 molecule corresponds to the nucleotide sequence of a 5'-EST that has been obtained from a human liver cDNA library. This 5'-EST is also part of the invention.

The invention also relates to isolated, purified, or recombinant polynucleotides comprising a contiguous span of at least 35, 40, 50, 60, 70, 80, 90, 100, 150, 200, 500, or 1000 nucleotides of the nucleotide sequence of SEQ ID No 2, or the complements thereof. Particularly preferred nucleic acids of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the following nucleotide positions of SEQ ID No 2: 1–78, 91–190, 208–229, 243–288, 301–328, 364–394, 409–457, 478–490, 505–508, 529–597, 616–633, 656–667, 682–688, 703–1188.

While this section is entitled "CIDE B cDNA Sequences," it should be noted that nucleic acid fragments of any size and sequence may also be comprised by the polynucleotides described in this section, flanking the genomic sequences of CIDE B on either side or between two or more such genomic sequences.

Coding Regions of CIDE B

The CIDE B open reading frame is contained in the corresponding mRNA of SEQ ID No 2 and is a further object of the present invention.

More precisely, the effective CIDE B coding sequence (CDS) is comprised between the nucleotide at position 80 (first nucleotide of the ATG codon) and the nucleotide at position 739 (end nucleotide of the TAA codon) of SEQ ID No 2. A purified or isolated polynucleotide comprising the CIDE B coding region defined above is another object of the invention.

The present invention concerns a purified or isolated nucleic acid encoding a human CIDE B protein, wherein said CIDE B protein comprises an amino acid sequence of SEQ ID No 3, a nucleotide sequence complementary thereto, a fragment or a variant thereof. The present invention also embodies isolated, purified, and recombinant polynucleotides which encode a polypeptides comprising a contiguous span of at least 35, 40, 50, or 100 amino acids of SEQ ID No 3. In a preferred embodiment, the present invention embodies isolated, purified, and recombinant polynucleotides which encode a polypeptides comprising a contiguous span of at least 8 amino acids, preferably at least 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 1–29, 47–70, 103–115, 124, 134, 169–185, and 203–219. In an additional preferred embodiment, the present invention embodies isolated, purified, and recombinant polynucleotides which encode a polypeptides comprising a contiguous span of at least 6 amino acids, preferably at least 8 to 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 7–11, 18–29, 47, 55–63, 70, 103–104, 111–115, 124, 134, 169–173, 181–185, and 203–219.

The above disclosed polynucleotide that contains the coding sequence of the CIDE B gene of the invention may be expressed in a desired host cell or a desired host organism, when this polynucleotide is placed under the control of suitable expression signals. The expression signals may be either the expression signals contained in the regulatory regions in the CIDE B gene of the invention or in contrast be exogenous regulatory nucleic sequences. Such a polynucleotide, when placed under the suitable expression signals, may also be inserted in a vector for its expression.

CIDE B Regulatory Sequences

As already mentioned hereinbefore, the genomic sequence of the CIDE B gene contains regulatory sequences both in the non-coding 5'-flanking region and in the non-coding 3'-flanking region that border the CIDE B coding region containing the exons of this gene.

The 5'-regulatory sequence of the CIDE B gene comprises the nucleotide sequence which is localized between the nucleotide in position 1 and the nucleotide in position 2802 of the nucleotide sequence of SEQ ID No 1. This polynucleotide would contain the promoter site.

The 3'-regulatory sequence of the CIDE B gene comprises the nucleotide sequence which is localized between the nucleotide in position 5556 and the nucleotide in position 10961 of the nucleotide sequence of SEQ ID No 1.

Polynucleotides derived from the CIDE B regulatory regions described above are useful in order to detect the presence of at least a copy of a nucleotide sequence of SEQ ID No 1, or a fragment or a variant thereof in a test sample.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. "5' regulatory region" refers to the nucleotide sequence located between positions 1 and 2802 of SEQ ID No 1. "3' regulatory region" refers to the nucleotide sequence located between positions 5556 and 10961 of SEQ ID No 1.

The invention also pertains to a purified or isolated nucleic acid comprising a polynucleotide having at least 70, 75, 80, 85, 90, or 95% nucleotide identity with the nucleotide sequence selected from the group consisting of the 5' and 3' regulatory regions, or a sequence complementary thereto or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

The promoter activity of the regulatory regions contained in the 5' regulatory region of CIDE B can be assessed as described below.

In order to identify the relevant biologically active polynucleotide fragments or variants of the 5' and 3' regulatory regions, the one skill in the art will refer to the book of Sambrook et al. (1989) which describes the use of a recombinant vector carrying a marker gene (i.e. beta galactosidase, chloramphenicol acetyl transferase, etc.) the expression of which will be detected when placed under the control of a biologically active polynucleotide fragments or variants of the 5' and 3' regulatory regions. Genomic sequences located upstream of the first exon of the CIDE B gene are cloned into a suitable promoter reporter vector, such as the pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, beta galactosidase, or green fluorescent protein. The sequences upstream the CIDE B coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequences within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has reduced or obliterated promoter activity, such as described, for example, by Coles et al. (1998). In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well-known to those skilled in the art and is described in WO 97/17359, U.S. Pat. No. 5,374,544, EP 582 796, U.S. Pat. Nos. 5,698,389, 5,643,746, 5,502,176, and 5,266,488.

The strength and the specificity of the promoter of the CIDE B gene can be assessed through the expression levels of a detectable polynucleotide operably linked to the CIDE B promoter in different types of cells and tissues. The detectable polynucleotide may be either a polynucleotide that specifically hybridizes with a predefined oligonucleotide probe, or a polynucleotide encoding a detectable protein, including a CIDE B polypeptide or a fragment or a variant thereof. This type of assay is well-known to those skilled in the art and is described in U.S. Pat. Nos. 5,502, 176, and 5,266,488.

Polynucleotides carrying the 5' and 3' regulatory regions of CIDE B coding region may be advantageously used to control the transcriptional and translational activity of an heterologous polynucleotide of interest.

Thus, the present invention also concerns a purified or isolated nucleic acid comprising a polynucleotide which is selected from the group consisting of the 5' and 3' regulatory regions of CIDE B, or a sequence complementary thereto or a biologically active fragment or variant thereof.

Preferred fragments of the 5' regulatory region of CIDE B have a length of about 1000 nucleotides, more particularly about 500 nucleotides, more preferably 200 nucleotides and most preferably about 100 nucleotides.

Preferred fragments of 3' regulatory region of CIDE B have a length of about 1000 nucleotides, more particularly about 500 nucleotides, more preferably 200 nucleotides and most preferably about 100 nucleotides.

By a "biologically active" polynucleotide derivative of the 5' and 3' regulatory regions of the CIDE B is intended a polynucleotide comprising or alternatively consisting in a fragment of said polynucleotide which is functional as a regulatory region for expressing a recombinant polypeptide or a recombinant polynucleotide in a recombinant cell host.

For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

These regulatory polynucleotides can also be prepared by nucleic acid chemical synthesis, as described elsewhere in the specification, where oligonucleotide probes or primers synthesis is disclosed.

The regulatory polynucleotides according to the invention may be advantageously part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-UTR of CIDE B, or a biologically active fragment or variant thereof.

A preferred 3'-regulatory polynucleotide of the invention includes a 3'-UTR of CIDE B, or a biologically active fragment or variant thereof. This preferred 3'-regulatory polynucleotide carries a polyadenylation site located between the nucleotide in position 1158 and the nucleotide in position 1163 of the nucleic acid of SEQ ID No 2.

The regulatory polynucleotides of the invention may be prepared from any of the nucleotide sequence of SEQ ID No 1 by cleavage using suitable restriction enzymes, as described for example in the book of Sambrook et al. (1989). The regulatory polynucleotides may also be prepared by digestion of any of SEQ ID No 1 by an exonuclease enzyme, such as for example Bal31 (Wabiko et al., 1986).

A further object of the invention consists of a purified or isolated nucleic acid comprising:
  a) a nucleic acid comprising the 5' regulatory region of CIDE B or a biologically active fragment or variant thereof;
  b) a polynucleotide encoding a desired polypeptide or nucleic acid operably linked to said 5' regulatory polynucleotide or its biologically active fragment or variant thereof;
  c) optionally, a nucleic acid comprising the 3' regulatory region of CIDE B or a biologically active fragment or variant thereof.

In a specific embodiment of the nucleic acid defined above, said nucleic acid includes the 5'-UTR of CIDE B, or a biologically active fragment or variant thereof. In a second specific embodiment of the nucleic acid defined above, said nucleic acid includes the 3'-UTR of CIDE B, or a biologically active fragment or variant thereof.

The 5' regulatory region of CIDE B, or its biologically active fragments or variants, is advantageously operably linked at the 5'-end of the polynucleotide encoding the desired polypeptide or polynucleotide.

The 3' regulatory region of CIDE B, or its biologically active fragments and variants, is advantageously placed at the 3'-end of the polynucleotide encoding the desired polypeptide or polynucleotide.

The desired polypeptide encoded by the above described nucleic acid may be of various nature or origin, encompassing proteins of prokaryotic or eukaryotic origin. Among the polypeptides expressed under the control of a CIDE B regulatory region, there may be cited bacterial, fungal or viral antigens. Also encompassed are eukaryotic proteins such as intracellular proteins, like "house keeping" proteins, membrane-bound proteins, like receptors, and secreted proteins like the numerous endogenous mediators such as cytokines. The desired polypeptide may be the CIDE B protein, especially the protein of the amino acid sequence of SEQ ID No 3, or a fragment or a variant thereof.

The desired nucleic acids encoded by the above described polynucleotide, usually a RNA molecule, may be complementary to a desired coding polynucleotide, for example to the CIDE B coding sequence, and thus useful as an antisense polynucleotide.

Such a polynucleotide may be included in a recombinant expression vector in order to express the desired polypeptide or the desired nucleic acid in host cell or in a host organism. Suitable recombinant vectors that contain a polynucleotide such as described hereinbefore are disclosed elsewhere in the specification.

Oligonucleotide Probes And Primers

Polynucleotides derived from the CIDE B gene are useful in order to detect the presence of at least a copy of a nucleotide sequence of SEQ ID No 1 or 2, or a fragment, complement, or variant thereof in a test sample.

Particularly preferred probes and primers of the invention include isolated, purified, or recombinant polynucleotides comprising a contiguous span of at least 35, 40, 50, 60, 70, 80, 90, 100, 150, 200, 500, or 1000 nucleotides of SEQ ID No 1 or the complements thereof. Further preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 1 or the complements thereof, wherein said contiguous span comprises at least 1, 2, 3, 5, or 10 of the following nucleotide positions of SEQ ID No 1: 1–1000, 1001–2000, 2001–3000, 3001–4000, 4001–5000, 5001–6000, 6001–7000, 7001–8000, 8001–9000, 9001–10000, 10001–10961.

Other preferred probes and primers of the invention include isolated, purified, or recombinant polynucleotides comprising a contiguous span of at least 35, 40, 50, 60, 70, 80, 90, 100, 150, 200, 500, or 1000 nucleotides of SEQ ID No 2 or the complements thereof. Additional preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID No 2 or the complements thereof, wherein said contiguous span comprises at least 1, 2, 3, 5, or 10 of the following nucleotide positions of SEQ ID No 2: 1–78, 91–190, 208–229, 243–288, 301–328, 364–394, 409–457, 478–490, 505–508, 529–597, 616–633, 656–667, 682–688, 703–1188.

Thus, the invention also relates to nucleic acid probes characterized in that they hybridize specifically, under the stringent hybridization conditions defined above, with a nucleic acid selected from the group consisting of the nucleotide sequences of SEQ ID Nos 1 and 2 or a variant thereof or a sequence complementary thereto.

In one embodiment the invention encompasses isolated, purified, and recombinant polynucleotides consisting of, or consisting essentially of a contiguous span of 8 to 50 nucleotides of any one of SEQ ID No 1 and the complement thereof wherein said span includes a CIDE B-related biallelic marker in said sequence; optionally, wherein said CIDE B-related biallelic marker is selected from the group consisting of the biallelic markers 12-73-49 and 12-74-38, and the complements thereof; optionally, wherein said contiguous span is 18 to 47 nucleotides in length and said biallelic marker is within 4 nucleotides of the center of said polynucleotide; optionally, wherein said polynucleotide consists of said contiguous span and said contiguous span is 25 nucleotides in length and said biallelic marker is at the center of said polynucleotide; optionally, wherein the 3' end of said contiguous span is present at the 3' end of said polynucleotide; and optionally, wherein the 3' end of said contiguous span is located at the 3' end of said polynucleotide and said biallelic marker is present at the 3' end of said polynucleotide. In a preferred embodiment, said probes comprises, consists of, or consists essentially of a sequence selected from the following sequences: P(12-73-49) and P(12-74-38) and the complementary sequences thereto.

In another embodiment the invention encompasses isolated, purified and recombinant polynucleotides comprising, consisting of, or consisting essentially of a contiguous span of 8 to 50 nucleotides of SEQ ID No 1, or the complements thereof, wherein the 3' end of said contiguous span is located at the 3' end of said polynucleotide, and wherein the 3' end of said polynucleotide is located within 20 nucleotides upstream of a CIDE B-related biallelic marker in said sequence; optionally, wherein said CIDE B-related biallelic marker is selected from the group consisting of the biallelic markers 12-73-49 and 12-74-38, and the complements thereof; optionally, wherein the 3' end of said polynucleotide is located 1 nucleotide upstream of said CIDE B-related biallelic marker in said sequence; and optionally, wherein said polynucleotide consists essentially of a sequence selected from the following sequences: D(12-73-49), D(12-74-38), E(12-73-49), and E(12-74-38).

In a further embodiment, the invention encompasses isolated, purified, or recombinant polynucleotides comprising, consisting of, or consisting essentially of a sequence selected from the following sequences: B(12-73), B(12-74), C(12-73), and C(12-74).

In an additional embodiment, the invention encompasses polynucleotides for use in hybridization assays, sequencing assays, and enzyme-based mismatch detection assays for determining the identity of the nucleotide at a CIDE B-related biallelic marker in SEQ ID No 1 or the complements thereof, as well as polynucleotides for use in amplifying segments of nucleotides comprising a CIDE B-related biallelic marker in SEQ ID No 1 or the complements thereof; optionally, wherein said CIDE B-related biallelic marker is selected from the group consisting of the biallelic markers 12-73-49 and 12-74-38, and the complements thereof.

A probe or a primer according to the invention has between 8 and 1000 nucleotides in length, or is specified to be at least 12, 15, 18, 20, 25, 35, 40, 50, 60, 70, 80, 100, 250, 500 or 1000 nucleotides in length. More particularly, the length of these probes and primers can range from 8, 10, 15, 20, or 30 to 100 nucleotides, preferably from 10 to 50, more preferably from 15 to 30 nucleotides. Shorter probes and primers tend to lack specificity for a target nucleic acid sequence and generally require cooler temperatures to form sufficiently stable hybrid complexes with the template. Longer probes and primers are expensive to produce and can sometimes self-hybridize to form hairpin structures. The appropriate length for primers and probes under a particular set of assay conditions may be empirically determined by one of skill in the art. A preferred probe or primer consists of a nucleic acid comprising a polynucleotide selected from the group of the nucleotide sequences of P(12-73-49) and P(12-74-38) and the complementary sequence thereto, B(12-73), B(12-74), C(12-73), C(12-74), D(12-73-49), D(12-74-38), E(12-73-49), and E(12-74-38), for which the respective locations in the sequence listing are provided in Tables 1, 2, 3 and 4.

The formation of stable hybrids depends on the melting temperature (Tm) of the DNA. The Tm depends on the length of the primer or probe, the ionic strength of the solution and the G+C content. The higher the G+C content of the primer or probe, the higher is the melting temperature because G:C pairs are held by three H bonds whereas A:T pairs have only two. The GC content in the probes of the invention usually ranges between 10 and 75%, preferably between 35 and 60%, and more preferably between 40 and 55%.

The primers and probes can be prepared by any suitable method, including, for example, cloning and restriction of appropriate sequences and direct chemical synthesis by a method such as the phosphodiester method of Narang et al.(1979), the phosphodiester method of Brown et al.(1979), the diethylphosphoramidite method of Beaucage et al.(1981) and the solid support method described in EP 0 707 592.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. Pat. application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988). In addition, the probes according to the present invention may have structural characteristics such that they allow the signal amplification, such structural characteristics being, for example, branched DNA probes as those described by Urdea et al. in 1991 or in the European patent No. EP 0 225 807 (Chiron).

A label can also be used to capture the primer, so as to facilitate the immobilization of either the primer or a primer extension product, such as amplified DNA, on a solid support. A capture label is attached to the primers or probes and can be a specific binding member which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the CIDE B gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also comprises a method for detecting the presence of a nucleic acid comprising a nucleotide sequence selected from a group consisting of SEQ ID Nos 1 and 2, a fragment or a variant thereof and a complementary sequence thereto in a sample, said method comprising the following steps of:
 a) bringing into contact a nucleic acid probe or a plurality of nucleic acid probes which can hybridize with a nucleotide sequence included in a nucleic acid selected form the group consisting of the nucleotide sequences of SEQ ID Nos 1 and 2, a fragment or a variant thereof and a complementary sequence thereto and the sample to be assayed; and
 b) detecting the hybrid complex formed between the probe and a nucleic acid in the sample.

The invention further concerns a kit for detecting the presence of a nucleic acid comprising a nucleotide sequence selected from a group consisting of SEQ ID Nos 1 and 2, a fragment or a variant thereof and a complementary sequence thereto in a sample, said kit comprising:
 a) a nucleic acid probe or a plurality of nucleic acid probes which can hybridize with a nucleotide sequence included in a nucleic acid selected form the group consisting of the nucleotide sequences of SEQ ID Nos 1 and 2, a fragment or a variant thereof and a complementary sequence thereto; and
 b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate. In a third preferred embodiment, the nucleic acid probe or the plurality of nucleic acid probes comprise either a sequence which is selected from the group consisting of the nucleotide sequences of of P(12-73-49) and P(12-74-38) and the complementary sequence thereto, B(12-73), B(12-74), C(12-73), C(12-74), D(12-73-49), D(12-74-38), E(12-73-49), and E(12-74-38) or a biallelic marker selected from the group consisting of the biallelic markers 12-73-49 and 12-74-38 and the complements thereto.

Oligonucleotide Arrays

A substrate comprising a plurality of oligonucleotide primers or probes of the invention may be used either for detecting or amplifying targeted sequences in the CIDE B gene and may also be used for detecting mutations in the coding or in the non-coding sequences of the CIDE B gene.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256.

In another embodiment of the oligonucleotide arrays of the invention, an oligonucleotide probe matrix may advantageously be used to detect mutations occurring in the CIDE B gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the CIDE B gene that have been identified according, for example to the technique used by Huang et al.(1996) or Samson et al.(1996).

Another technique that is used to detect mutations in the CIDE B gene is the use of a high-density DNA array. Each oligonucleotide probe constituting a unit element of the high density DNA array is designed to match a specific subsequence of the CIDE B genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the CIDE B gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. in 1996.

Consequently, the invention concerns an array of nucleic acid molecules comprising at least one polynucleotide described above as probes and primers. Preferably, the invention concerns an array of nucleic acid comprising at least two polynucleotides described above as probes and primers.

A further object of the invention consists of an array of nucleic acid sequences comprising either at least one of the sequences selected from the group consisting of P(12-73-49), P(12-74-38), B(12-73), B(12-74), C(12-73), C(12-74), D(12-73-49), D(12-74-38), E(12-73-49), E(12-73-49), and E(12-74-38), the sequences complementary thereto, a fragment thereof of at least 8, 10, 12, 15, 18, 20, 25, 30, or 40 consecutive nucleotides thereof, and at least one sequence comprising a biallelic marker selected from the group consisting of the biallelic markers 12-73-49 and 12-74-38 and the complements thereto.

The invention also pertains to an array of nucleic acid sequences comprising either at least two of the sequences selected from the group consisting of P(12-73-49), P(12-74-38), B(12-73), B(12-74), C(12-73), C(12-74), D(12-73-49), D(12-74-38), E(12-73-49), and E(12-74-38), the sequences complementary thereto, a fragment thereof of at least 8 consecutive nucleotides thereof, and at least two sequences comprising a biallelic marker selected from the group consisting of the biallelic markers 12-73-49 and 12-74-38 and the complements thereof.

Amplification of The CIDE B Gene.
DNA Extraction

As for the source of the genomic DNA to be subjected to analysis, any test sample can be foreseen without any particular limitation. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens including tumor and non-tumor tissue and lymph node tissues; bone marrow aspirates and fixed cell specimens. The preferred source of genomic DNA used in the context of the present invention is from peripheral venous blood of each donor.

The techniques of DNA extraction are well-known to the skilled technician. Such techniques are described notably by Lin et al. (1998) and by Mackey et al. (1998).

DNA Amplification

Amplification techniques that can be used in the context of the present invention include, but are not limited to, the ligase chain reaction (LCR) described in EP-A-320 308, WO 9320227 and EP-A439 182, the polymerase chain reaction (PCR, RT-PCR) and techniques such as the nucleic acid sequence based amplification (NASBA) described in Guatelli J. C., et al.(1990) and in Compton J.(1991), Q-beta amplification as described in European Patent Application No 4544610, strand displacement amplification as described in Walker et al.(1996) and EP A 684 315 and, target mediated amplification as described in PCT Publication WO 9322461.

LCR and Gap LCR are exponential amplification techniques, both depend on DNA ligase to join adjacent primers annealed to a DNA molecule. In Ligase Chain Reaction (LCR), probe pairs are used which include two primary (first and second) and two secondary (third and fourth) probes, all of which are employed in molar excess to target. The first probe hybridizes to a first segment of the target strand and the second probe hybridizes to a second segment of the target strand, the first and second segments being contiguous so that the primary probes abut one another in 5' phosphate-3'hydroxyl relationship, and so that a ligase can covalently fuse or ligate the two probes into a fused product. In addition, a third (secondary) probe can hybridize to a portion of the first probe and a fourth (secondary) probe can hybridize to a portion of the second probe in a similar abutting fashion. Of course, if the target is initially double stranded, the secondary probes also will hybridize to the target complement in the first instance. Once the ligated strand of primary probes is separated from the target strand, it will hybridize with the third and fourth probes, which can be ligated to form a complementary, secondary ligated product. It is important to realize that the ligated products are functionally equivalent to either the target or its complement. By repeated cycles of hybridization and ligation, amplification of the target sequence is achieved. A method for multiplex LCR has also been described (WO 9320227). Gap LCR (GLCR) is a version of LCR where the probes are not adjacent but are separated by 2 to 3 bases.

For amplification of mRNAs, it is within the scope of the present invention to reverse transcribe mRNA into cDNA followed by polymerase chain reaction (RT-PCR); or, to use a single enzyme for both steps as described in U.S. Pat. No. 5,322,770 or, to use Asymmetric Gap LCR (RT-AGLCR) as described by Marshall et al.(1994). AGLCR is a modification of GLCR that allows the amplification of RNA.

The PCR technology is the preferred amplification technique used in the present invention. A variety of PCR techniques are familiar to those skilled in the art. For a review of PCR technology, see White (1997) and the publication entitled "PCR Methods and Applications" (1991, Cold Spring Harbor Laboratory Press). In each of these PCR procedures, PCR primers on either side of the nucleic acid sequences to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195; 4,683,202; and 4,965,188.

The present invention also relates to a method for the amplification of a human CIDE B gene sequence, particularly of a portion of the genomic sequence of SEQ ID No 1 or of the cDNA sequence of SEQ ID No 2, or a variant thereof in a test sample, said method comprising the steps of:

a) contacting a test sample suspected of containing the targeted CIDE B gene sequence comprised in a nucleotide sequence selected from a group consisting of SEQ ID Nos 1 and 2, or fragments or variants thereof with amplification reaction reagents comprising a pair of amplification primers as described above and located on either side of the polynucleotide region to be amplified, and b) optionally, detecting the amplification products.

The invention also concerns a kit for the amplification of a human CIDE B gene sequence, particularly of a portion of the genomic sequence of SEQ ID No 1 or of the cDNA sequence of SEQ ID No 2, or a variant thereof in a test sample, wherein said kit comprises:

a) a pair of oligonucleotide primers located on either side of the CIDE B region to be amplified;

b) Optionally, the reagents necessary for performing the amplification reaction.

In one specific embodiment of the above amplification method and kit, the amplification primers are selected from the group consisting of the polynucleotides B(12-73), B(12-74), C(12-73), C(12-74), D(12-73-49), D(12-74-38), E(12-73-49), and E(12-74-38).

In another embodiment of the above amplification method and kit, the amplification product is detected by hybridization with a labeled probe having a sequence which is complementary to the amplified region.

CIDE B Polypeptide And Peptide Fragments Thereof

It is now easy to produce proteins in high amounts by genetic engineering techniques through expression vectors such as plasmids, phages or phagemids. The polynucleotide that code for one the polypeptides of the present invention is inserted in an appropriate expression vector in order to produce the polypeptide of interest in vitro.

Thus, the present invention also concerns a method for producing one of the polypeptides described herein, and especially a polypeptide of SEQ ID No 3 or a fragment or a variant thereof, wherein said method comprises the steps of:

a) culturing, in an appropriate culture medium, a cell host previously transformed or transfected with the recombinant vector comprising a nucleic acid encoding a CIDE B polypeptide, or a fragment or a variant thereof;

b) harvesting the culture medium thus conditioned or lyse the cell host, for example by sonication or by an osmotic shock;

c) separating or purifying, from the said culture medium, or from the pellet of the resultant host cell lysate the thus produced polypeptide of interest.

d) Optionally characterizing the produced polypeptide of interest.

In a specific embodiment of the above method, step a) is preceded by a step wherein the nucleic acid coding for a CIDE B polypeptide, or a fragment or a variant thereof, is inserted in an appropriate vector, optionally after an appropriate cleavage of this amplified nucleic acid with one or several restriction endonucleases. The nucleic acid coding for a CIDE B polypeptide or a fragment or a variant thereof may be the resulting product of an amplification reaction using a pair of primers according to the invention (by SDA, TAS, 3SR NASBA, TMA etc.).

The polypeptides according to the invention may be characterized by binding onto an immunoaffinity chromatography column on which polyclonal or monoclonal antibodies directed to a polypeptide of SEQ ID No 3, or a fragment or a variant thereof, have previously been immobilized.

Purification of the recombinant proteins or peptides according to the present invention may be carried out by passage onto a Nickel or Cupper affinity chromatography column. The Nickel chromatography column may contain the Ni-NTA resin (Porath et al., 1975).

The polypeptides or peptides thus obtained may be purified, for example by high performance liquid chromatography, such as reverse phase and/or cationic exchange HPLC, as described by Rougeot et al. (1994). The reason to prefer this kind of peptide or protein purification is the lack of byproducts found in the elution samples which renders the resultant purified protein or peptide more suitable for a therapeutic use.

In a preferred embodiment, the CIDE B polypeptide comprises an amino acid sequence of SEQ ID No 3 or a fragment or a variant thereof.

The CIDE B polypeptide of the amino acid sequence of SEQ ID No 3 has 219 amino acids in length.

The human CIDE B protein presents 85% of identity with the murine CIDE B. This level of identity shows that the protein of the present invention is the human homologue of the murine CIDE B. In contrast, the human CIDE B protein of the invention presents only 42% of identity with the human CIDE A protein.

The invention also encompasses a purified, isolated, or recombinant polypeptides comprising an amino acid sequence having at least 90, 95, 98 or 99% amino acid identity with the amino acid sequence of SEQ ID No 3 or a fragment thereof.

In a preferred embodiment, the CIDE B polypeptide comprises an amino acid sequence of SEQ ID No 3 or a fragment or a variant thereof. The present invention also embodies isolated, purified, and recombinant polypeptides comprising a contiguous span of at least 35, 40, 50, 100, 150 or 200 amino acids of SEQ ID No 3. The present invention also embodies isolated, purified, and recombinant polypeptides comprising a contiguous span of at least 8 amino acids, preferably at least 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 1–29, 47–70, 103–115, 124, 134, 169–185, and 203–219. Furthermore, the present invention embodies isolated, purified, and recombinant polypeptides comprising a contiguous span of at least 6 amino acids, preferably at least 8 to 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 7–11, 18–29, 47, 55–63, 70, 103–104, 111–115, 124, 134, 169–173, 181–185, and 203–219.

Particular regions of the CIDE B polypeptide have interesting features. Two large hydrophilic and antigenic regions respectively begin at the amino acids in position 8 (N) and 79 (E), and respectively end at the amino acids in position 58 (E) and 146 (L) of the amino acid sequence of CIDE B.

Four small regions having a good probability to be exposed to the outer environment are the amino acid sequences beginning at positions 31 (A), 43 (H), 121 (G), and 138 (V) and respectively ending at positions 37 (P), 47 (I), 128 (S) 144 (R) and of the CIDE B protein.

A further object of the present invention concerns a purified or isolated polypeptide which is encoded by a nucleic acid selected from the group consisting of SEQ ID Nos 1 and 2 or fragments or variants thereof.

The invention also encompasses a purified or isolated nucleic acid encoding a CIDE B protein having the amino acid sequence of SEQ ID No 3, or a peptide fragment or variant thereof.

In a second preferred embodiment, a mutated CIDE B polypeptide comprises amino acid changes with at least one amino acid deletion, substitution or addition, preferably from 1 to 10, 20 or 30 amino acid deletions, substitutions or additions. The amino acid substitutions are generally non conservative in terms of polarity, charge, hydrophilicity properties of the substitute amino acid when compared with the native amino acid. The amino acid changes occurring in such a mutated CIDE B polypeptide may be determinant for the biological activity or for the capacity of the mutated CIDE B polypeptide to be recognized by antibodies raised against a native CIDE B.

Such a mutated CIDE B protein may be the target of diagnostic tools, such as specific monoclonal or polyclonal antibodies, useful for detecting the mutated CIDE B protein in a sample.

The invention also encompasses a CIDE B polypeptide or a fragment or a variant thereof in which at least one peptide bound has been modified as described in the "Definitions" section.

Antibodies that Bind CIDE B Polypeptides of the Invention

Any CIDE B polypeptide or whole protein may be used to generate antibodies capable of specifically binding to an expressed CIDE B protein or fragments thereof as described.

One antibody composition of the invention is capable of specifically binding or specifically bind to the variant of the CIDE B protein of SEQ ID No 3. For an antibody composition to specifically bind to CIDE B, it must demonstrate at least a 5%, 10%, 15%, 20%, 25%, 50%, or 100% greater binding affinity for CIDE B protein than for another protein in an ELISA, RIA, or other antibody-based binding assay.

In a preferred embodiment, the invention concerns antibody compositions, either polyclonal or monoclonal, capable of selectively binding, or selectively bind to an epitope containing a polypeptide comprising a contiguous span of at least 35, 40, 50, 100, 150 or 200 amino acids of SEQ ID No 3; Optionally said epitope contains a polypeptide comprising a contiguous span of at least 8 amino acids, preferably at least 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 1–29, 47–70, 103–115, 124, 134, 169–185, and 203–219; Optionally said epitope contains a polypeptide comprising a contiguous span of at least 6 amino acids, preferably at least 8 to 10 amino acids, more preferably at least 12, 15, 20. 25, 30, 40, 50, 100, 150 or 200 amino acids of SEQ ID No 3, wherein said contiguous span includes at least 1, 2, 3, 5 or 10 of the following amino acid positions: 7–11, 18–29, 47, 55–63, 70, 103–104, 111–115, 124, 134, 169–173, 181–185, and 203–219.

The invention also concerns a purified or isolated antibody capable of specifically binding to a mutated CIDE B protein or to a fragment or variant thereof comprising an epitope of the mutated CIDE B protein. In another preferred embodiment, the present invention concerns an antibody capable of binding to a polypeptide comprising at least 10 consecutive amino acids of a CIDE B protein and including at least one of the amino acids which can be encoded by the trait causing mutations.

In a preferred embodiment, the invention concerns the use in the manufacture of antibodies of a polypeptide comprising a contiguous span of at least 35, 40, 50, 100, 150 or 200 amino acids of SEQ ID No 3; Optionally said polypeptide comprises a contiguous span of at least 8 amino acids, preferably at least 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 1–29, 47–70, 103–115, 124, 134, 169–185, and 203–219; Optionally said polypeptide comprises a contiguous span of at least 6 amino acids, preferably at least 8 to 10 amino acids, more preferably at least 12, 15, 20, 25, 30, 40, 50, 100, 150 or 200 amino acids of SEQ ID No 3, wherein said contiguous span includes at least 1, 2, 3, 5 or 10 of the following amino acid positions: 7–11, 18–29, 47, 55–63, 70, 103–104, 111–115, 124, 134, 169–173, 181–185, and 203–219.

The preferred fragments of CIDE B protein used for the preparation of anti-human CIDE B antibodies comprise, or are comprised in, the amino acid sequence located between the positions 8 and 58 of SEQ ID No 3 and between the positions 79 and 146 of SEQ ID No 3. More particularly, the fragments of CIDE B protein used for the preparation of anti-human CIDE B antibodies comprise the amino acid sequence located between the positions 31 and 37, 43 and 47, 121 and 128, and 138 and 144 of the polypeptide sequence of SEQ ID No 3.

The antibodies of the invention may be labeled by any one of the radioactive, fluorescent or enzymatic labels known in the art.

The CIDE B polypeptide of SEQ ID No 3 or a fragment thereof can be used for the preparation of polyclonal or monoclonal antibodies.

The CIDE B polypeptide expressed from a DNA sequence comprising at least one of the nucleic acid sequences of SEQ ID Nos 1 and 2 may also be used to generate antibodies capable of specifically binding to the CIDE B polypeptide of SEQ ID No 3 a fragment thereof.

The antibodies may be prepared from hybridomas according to the technique described by Kohler and Milstein in 1975. The polyclonal antibodies may be prepared by immunization of a mammal, especially a mouse or a rabbit, with a polypeptide according to the invention that is combined with an adjuvant of immunity, and then by purifying of the specific antibodies contained in the serum of the immunized animal on a affinity chromatography column on which has previously been immobilized the polypeptide that has been used as the antigen.

The present invention also includes, chimeric single chain Fv antibody fragments (Martineau et al., 1998), antibody fragments obtained through phage display libraries (Ridder et al., 1995; Vaughan et al., 1995) and humanized antibodies (Reinmann et al., 1997; Leger et al., 1997).

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

Consequently, the invention is also directed to a method for detecting specifically the presence of a CIDE B polypeptide according to the invention in a biological sample, said method comprising the following steps:

a) bringing into contact the biological sample with a polyclonal or monoclonal antibody that specifically binds a CIDE B polypeptide comprising an amino acid sequence of SEQ ID No 3, or to a peptide fragment or variant thereof; and b) detecting the antigen-antibody complex formed.

The invention also concerns a diagnostic kit for detecting in vitro the presence of a CIDE B polypeptide according to the present invention in a biological sample, wherein said kit comprises:

a) a polyclonal or monoclonal antibody that specifically binds a CIDE B polypeptide comprising an amino acid sequence of SEQ ID No 3, or to a peptide fragment or variant thereof, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself.

Biallelic Markers of The CIDE B Gene
Identification of Biallelic Markers

There are two preferred methods through which the biallelic markers of the present invention can be generated. In a first method, DNA samples from unrelated individuals are pooled together, following which the genomic DNA of interest is amplified and sequenced. The nucleotide sequences thus obtained are then analyzed to identify significant polymorphisms.

One of the major advantages of this method resides in the fact that the pooling of the DNA samples substantially reduces the number of DNA amplification reactions and sequencing which must be carried out. Moreover, this method is sufficiently sensitive so that a biallelic marker obtained therewith usually shows a sufficient degree of informativeness for conducting association studies.

In a second method for generating biallelic markers, the DNA samples are not pooled and are therefore amplified and sequenced individually. The resulting nucleotide sequences obtained are then also analyzed to identify significant polymorphisms.

It will readily be appreciated that when this second method is used, a substantially higher number of DNA amplification reactions must be carried out. It will further be appreciated that including such potentially less informative biallelic markers in association studies to identify potential genetic associations with a trait may allow in some cases the direct identification of causal mutations, which may, depending on their penetrance, be rare mutations. This method is usually preferred when biallelic markers need to be identified in order to perform association studies within candidate genes.

In both methods, the genomic DNA samples from which the biallelic markers of the present invention are generated are preferably obtained from unrelated individuals corresponding to a heterogeneous population of known ethnic background, or from familial cases.

The number of individuals from whom DNA samples are obtained can vary substantially, preferably from about 10 to about 1000, preferably from about 50 to about 200 individuals. It is usually preferred to collect DNA samples from at least about 100 individuals in order to have sufficient polymorphic diversity in a given population to generate as many markers as possible and to generate statistically significant results.

As for the source of the genomic DNA to be subjected to analysis, any test sample can be foreseen without any particular limitation. The preferred source of genomic DNA used in the context of the present invention is the peripheral venous blood of each donor.

The techniques of DNA extraction are well-known to the skilled technician. Details of a preferred embodiment are provided in Example 1.

DNA samples can be pooled or unpooled for the amplification step. DNA amplification techniques are well-known to those skilled in the art. The PCR technology is the preferred amplification technique used in the present invention. A typical example of a PCR reaction suitable for the purposes of the present invention is provided in Example 2.

The primers used for the amplification are as defined above. Preferred primers of the invention include the nucleotide sequences of B(12-73), B(12-74), C(12-73), C(12-74), D(12-73-49), D(12-74-38), E(12-73-49), and E(12-74-38). More preferred primers of the invention include the nucleotide sequences of B(12-73), B(12-74), C(12-73), and C(12-74).

The amplification products generated as described above with the primers of the invention are then sequenced using methods known and available to the skilled technician. Preferably, the amplified DNA is subjected to automated dideoxy terminator sequencing reactions using a dye-primer cycle sequencing protocol. Following gel image analysis and DNA sequence extraction, sequence data are automatically processed with adequate software to assess sequence quality.

The presence of biallelic sites are detected among individual or pooled amplified fragment sequences. Polymorphism search is based on the presence of superimposed peaks in the electrophoresis pattern. These peaks which present distinct colors correspond to two different nucleotides at the same position on the sequence. The polymorphism has to be detected on both strands for validation.

The biallelic markers of the present invention are disclosed in Table 2 of Example 3. Their location on the CIDE B gene is indicated as features in SEQ ID No 1. The pair of amplification primers are listed in the sequence listing in features of the SEQ ID No 1 and are described in Table 1 of example 2, these primers allowing the amplification of a nucleic acid containing the polymorphic base that defines this biallelic marker.

In the present invention, the biallelic markers can be defined by nucleotide sequences corresponding to oligonucleotides of 47 bases in length comprising at the middle one of the polymorphic base. More particularly, the biallelic markers can be defined by the polynucleotides P(12-73-49) and P(12-74-38).

The biallelic markers 12-73-49 and 12-74-38 are located in the 3' regulatory region and form part of the present invention.

The biallelic markers contained in the human CIDE B gene are useful tools to perform association studies between the statistically significant occurrence of an allele of said biallelic marker in the genome of an individual and a specific phenotype, including a phenotype consisting of a disorder related to apoptosis such as cancer or AIDS. The biallelic markers of the invention can also be used, for example, for the generation of genetic map, the linkage analysis.

Genotyping of Biallelic Markers

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods which do not require amplification are also encompassed by the present genotyping methods. Methods well-known to those skilled in the art that can be used to detect biallelic polymorphisms include methods such as, conventional dot blot analyzes, single strand conformational polymorphism analysis (SSCP) described by Orita et al. (1989), denaturing gradient gel electrophoresis (DGGE), heteroduplex analysis, mismatch cleavage detection, and other conventional techniques as described in Sheffield et al. (1991), White et al. (1992), Grompe et al. (1989 and 1993). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, enzyme-based mismatch detection assay, or hybridization assay. The following is a description of some preferred methods. A highly preferred method is the microsequencing technique. The term "sequencing" is generally used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing as described above.

Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers which, hybridize just upstream of the polymorphic base of interest in the target nucleic acid. A polymerase is used to specifically extend the 3' end of the primer with one single ddNTP (chain terminator) complementary to the nucleotide at the polymorphic site. Next the identity of the incorporated nucleotide is determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously. An example of a typical microsequencing procedure that can be used in the context of the present invention is provided in Example 4.

Different approaches can be used for the labeling and detection of ddNTPs. A homogeneous phase detection method based on fluorescence resonance energy transfer has been described by Chen and Kwok (1997) and Chen et al. (1997). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, 1997).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template. For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, 1994) or linked to fluorescein (Livak and Hainer, 1994). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate). Other possible reporter-detection pairs include: ddNTP linked to dinitrophenyl (DNP) and anti-DNP alkaline phosphatase conjugate (Harju et al., 1993) or biotinylated ddNTP and horseradish peroxidase-conjugated streptavidin with o-phenylenediamine as a substrate (WO 92/15712). As yet another alternative solid-phase microsequencing procedure, Nyren et al. (1993) described a method relying on the detection of DNA polymerase activity by an enzymatic luminometric inorganic pyrophosphate detection assay (ELIDA).

Pastinen et al. (1997) describe a method for multiplex detection of single nucleotide polymorphism in which the solid phase minisequencing principle is applied to an oligonucleotide array format. High-density arrays of DNA probes attached to a solid support (DNA chips) are further described below.

In one aspect the present invention provides polynucleotides and methods to genotype one or more biallelic markers of the present invention by performing a microsequencing assay. Preferred microsequencing primers include the nucleotide sequences D(12-73-49), D(12-74-38), E(12-73-49), and E(12-74-38). It will be appreciated that the microsequencing primers listed in Example 4 are merely exemplary and that, any primer having a 3' end immediately adjacent to the polymorphic nucleotide may be used. Similarly, it will be appreciated that microsequencing analysis may be performed for any biallelic marker or any combination of biallelic markers of the present invention. One aspect of the present invention is a solid support which includes one or more microsequencing primers listed in Example 4, or fragments comprising at least 8, 12, 15, 20, 25, 30, 40, or 50 consecutive nucleotides thereof, to the extent that such lengths are consistent with the primer described, and having a 3' terminus immediately upstream of the corresponding biallelic marker, for determining the identity of a nucleotide at a biallelic marker site.

3) Mismatch Detection Assays Based on Polymerases and Ligases

In one aspect the present invention provides polynucleotides and methods to determine the allele of one or more biallelic markers of the present invention in a biological sample, by mismatch detection assays based on polymerases and/or ligases. These assays are based on the specificity of polymerases and ligases. Polymerization reactions places particularly stringent requirements on correct base pairing of the 3' end of the amplification primer and the joining of two oligonucleotides hybridized to a target DNA sequence is quite sensitive to mismatches close to the ligation site, especially at the 3' end. Methods, primers and various parameters to amplify DNA fragments comprising biallelic markers of the present invention are further described above in "Amplification of DNA Fragments Comprising Biallelic Markers".

Allele Specific Amplification Primers

Discrimination between the two alleles of a biallelic marker can also be achieved by allele specific amplification, a selective strategy, whereby one of the alleles is amplified without amplification of the other allele. For allele specific amplification, at least one member of the pair of primers is sufficiently complementary with a region of a CIDE B gene comprising the polymorphic base of a biallelic marker of the present invention to hybridize therewith and to initiate the amplification. Such primers are able to discriminate between the two alleles of a biallelic marker.

This is accomplished by placing the polymorphic base at the 3' end of one of the amplification primers. Because the extension forms from the 3' end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well within the ordinary skill in the art.

Ligation/Amplification Based Methods

The "Oligonucleotide Ligation Assay" (OLA) uses two oligonucleotides which are designed to be capable of hybridizing to abutting sequences of a single strand of a target molecules. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. (1990). In this method, PCR is used to achieve the exponential amplification of target DNA, which is then detected using OLA.

Other amplification methods which are particularly suited for the detection of single nucleotide polymorphism include LCR (ligase chain reaction), Gap LCR (GLCR) which are described above in "DNA Amplification". LCR uses two pairs of probes to exponentially amplify a specific target. The sequences of each pair of oligonucleotides, is selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained.

Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include the probes defined herein. Any hybridization assay may be used including Southern hybridization, Northern hybridization, dot blot hybridization and solid-phase hybridization (see Sambrook et al., 1989).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms, Allele-specific probes are often used in pairs, one member of a pair showing perfect match to a target sequence containing the original allele and the other showing a perfect match to the target sequence containing the alternative allele. Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., 1989). Stringent conditions are sequence dependent and will be different in different circumstances. Generally, stringent conditions are selected to be about 5° C. lower than the thermal melting point (Tm) for the specific sequence at a defined ionic strength and pH. Although such hybridization can be performed in solution, it is preferred to employ a solid-phase hybridization assay. The target DNA comprising a biallelic marker of the present invention may be amplified prior to the hybridization reaction. The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., 1998). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence energy transfer. Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995). In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., 1998).

The polynucleotides provided herein can be used to produce probes which can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. Preferred probes comprise a nucleotide sequence selected from the group consisting of amplicons listed in Table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. Preferred probes comprise a nucleotide sequence selected from the group consisting of P(12-73-49) and P(12-74-38) and the sequences complementary thereto. In preferred embodiments the polymorphic base(s) are within 5, 4, 3, 2, 1, nucleotides of the center of the said polynucleotide, more preferably at the center of said polynucleotide.

Preferably the probes of the present invention are labeled or immobilized on a solid support. Labels and solid supports are further described in "Oligonucleotide Probes and Primers". The probes can be non-extendable as described in "Oligonucleotide Probes and Primers".

By assaying the hybridization to an allele specific probe, one can detect the presence or absence of a biallelic marker allele in a given sample. High-Throughput parallel hybridization in array format is specifically encompassed within "hybridization assays" and are described below.

5) Hybridization To Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA 1 gene, in *S. cerevisiae* mutant strains, and in the protease gene of HIV-1 virus (Hacia et al., 1996; Shoemaker et al., 1996; Kozal et al., 1996). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual which, target sequences include a polymorphic marker. EP 785280 describes a tiling strategy for the detection of single nucleotide polymorphisms. Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers. For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These monosubstituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artefactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In further embodiments, the chip may comprise an array including at least one of the sequences selected from the group consisting of amplicons listed in table 1 and the sequences complementary thereto, or a fragment thereof, said fragment comprising at least about 8 consecutive nucleotides, preferably 10, 15, 20, more preferably 25, 30, 40, 47, or 50 consecutive nucleotides and containing a polymorphic base. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides of the invention. Solid supports and polynucleotides of the present invention attached to solid supports are further described in "Oligonucleotide Probes And Primers".

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts.

For genotyping biallelic markers, the microfluidic system may integrate nucleic acid amplification, microsequencing, capillary electrophoresis and a detection method such as laser-induced fluorescence detection.

Expression of A Regulatory or Coding Polynucleotide of CIDE B

Any of the regulatory polynucleotides or the coding polynucleotides of the invention may be inserted into recombinant vectors for expression in a recombinant host cell or a recombinant host organism.

Thus, the present invention also encompasses a family of recombinant vectors that contains either a regulatory polynucleotide selected from the group consisting of any one of the regulatory polynucleotides derived from the CIDE B genomic sequence, or a coding polynucleotide from the CIDE B genomic sequence. Consequently, the present invention further deals with a recombinant vector comprising either a regulatory polynucleotide contained in the nucleic acid of SEQ ID No 1, or a polynucleotide comprising the CIDE B coding sequence, or both.

In a first preferred embodiment, a recombinant vector of the invention is used as an expression vector: (a) the CIDE B regulatory sequence comprised therein drives the expression of a coding polynucleotide operably linked thereto; (b) the CIDE B coding sequence is operably linked to regulation sequences allowing its expression in a suitable cell host and/or host organism.

In a second preferred embodiment, a recombinant vector of the invention is used to amplify the inserted polynucleotide derived from a CIDE B genomic sequence selected from the group consisting of the nucleic acids of SEQ ID No 1 or a CIDE B cDNA in a suitable cell host, this polynucleotide being amplified at every time that the recombinant vector replicates.

More particularly, the present invention relates to expression vectors which include nucleic acids encoding a CIDE B protein, preferably the CIDE B protein of the amino acid sequence of SEQ ID No 3 or variants or fragments thereof, under the control of a regulatory sequence selected among the CIDE B regulatory polynucleotides, or alternatively under the control of an exogenous regulatory sequence.

A recombinant expression vector comprising a nucleic acid selected from the group consisting of the 5' regulatory region, or biologically active fragments or variants thereof, is also part of the present invention.

Generally, a recombinant vector of the invention may comprise any of the polynucleotides described herein, including regulatory sequences, and coding sequences, as well as any CIDE B primer or probe as defined above. More particularly, the recombinant vectors of the present invention can comprise any of the polynucleotides described in the "CIDEB cDNA Sequences" section, the "Coding Regions of CIDE B" section, "Genomic sequence of CIDE B" section and the "Oligonucleotide Probes And Primers" section.

Some of the elements which can be found in the vectors of the present invention are described in further detail in the following sections.

Vectors

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may consist of a chromosomal, non-chromosomal and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, and (3) appropriate transcription initiation and termination sequences. Structural units intended for use in yeast or eukaryotic expression systems preferably include a leader sequence enabling extracellular secretion of translated protein by a host cell. Alternatively, where a recombinant protein is expressed without a leader or transport sequence, it may include an N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium.

The selectable marker genes for selection of transformed host cells are preferably dihydrofolate reductase or neomycin resistance for eukaryotic cell culture, TRPI for S. cerevisiae or tetracycline, rifampicin or ampicillin resistance in E. coli, or levan saccharase for mycobacteria.

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM1 (Promega Biotec, Madison, Wis., USA).

Large numbers of suitable vectors and promoters are known to those of skill in the art, and commercially available, such as bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); or eukaryotic vectors: pWLNEO, pSV2CAT, pOG44, pXT1, pSG (Stratagene); pSVK3, pBPV, pMSG, pSVL (Pharmacia); baculovirus transfer vector pVL1392/1393 (Pharmingen); pQE-30 (QIAexpress).

A suitable vector for the expression of the CIDE B polypeptide of SEQ ID No 3 or fragments or variants thereof is a baculovirus vector that can be propagated in insect cells and in insect cell lines. A specific suitable host vector system is the pVL 1392/1393 baculovirus transfer vector (Pharmingen) that is used to transfect the SF9 cell line (ATCC NoCRL 1711) which is derived from *Spodoptera frugiperda*.

Other suitable vectors for the expression of the CIDE B polypeptide of SEQ ID No 3 or fragments or variants thereof in a baculovirus expression system include those described by Chai et al. (1993), Vlasak et al. (1983) and Lenhard et al. (1996).

Mammalian expression vectors will comprise an origin of replication, a suitable promoter and enhancer, and also any necessary ribosome binding sites, polyadenylation site, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

Promoters

The suitable promoter regions used in the expression vectors according to the present invention are chosen taking into account the cell host in which the heterologous gene has to be expressed.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Preferred bacterial promoters are the LacI, LacZ, the T3 or T7 bacteriophage RNA polymerase promoters, the polyhedrin promoter, or the p10 protein promoter from baculovirus (Kit Novagen) (Smith et al., 1983; O'Reilly et al., 1992), the lambda PR promoter or also the trc promoter.

Promoter regions can be selected from any desired gene using, for example, CAT (chloramphenicol transferase) vectors and more preferably pKK232-8 and pCM7 vectors. Particularly preferred bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

The choice of a promoter is well within the ability of a person skilled in the field of genetic egineering. For example, one may refer to the book of Sambrook et al. (1989) or also to the procedures described by Fuller et al. (1996).

The vector containing the appropriate DNA sequence as described above, more preferably CIDE B gene regulatory polynucleotide, a polynucleotide encoding the CIDE B polypeptide of SEQ ID No 3 or both of them, can be utilized to transform an appropriate host to allow the expression of the desired polypeptide or polynucleotide.

Other types of Vectors

The in vivo expression of a CIDE B polypeptide of SEQ ID No No 3 or fragments or variants thereof may be useful in order to correct a genetic defect related to the expression of the native gene in a host organism or to the production of a biologically inactive CIDE B protein.

Consequently, the present invention also deals with recombinant expression vectors mainly designed for the in vivo production of the CIDE B polypeptide of SEQ ID No No 3 or fragments or variants thereof by the introduction of the appropriate genetic material in the organism of the patient to be treated. This genetic material may be introduced in vitro in a cell that has been previously extracted from the organism, the modified cell being subsequently reintroduced in the said organism, directly in vivo into the appropriate tissue.

By <<vector>> according to this specific embodiment of the invention is intended either a circular or a linear DNA molecule.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect.

In a specific embodiment, the invention provides a composition for the in vivo production of the CIDE B protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

Compositions comprising a polynucleotide are described in PCT application N° WO 90/11092 (Vical Inc.) and also in PCT application N° WO 95/11307 (Institut Pasteur, INSERM, Universite d'Ottawa) as well as in the articles of Tacson et al. (1996) and of Huygen et al. (1996).

The amount of vector to be injected to the desired host organism varies according to the site of injection. As an indicative dose, it will be injected between 0.1 and 100 μg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired CIDE B polypeptide or the desired fragment thereof is reintroduced into the animal body in order to deliver the recombinant protein within the body either locally or systemically.

In one specific embodiment, the vector is derived from an adenovirus. Preferred adenovirus vectors according to the invention are those described by Feldman and Steg (1996) or Ohno et al. (1994). Another preferred recombinant adenovirus according to this specific embodiment of the present invention is the human adenovirus type 2 or 5 (Ad 2 or Ad 5) or an adenovirus of animal origin (French patent application N° FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR659 and VR-728). Other preferred retroviral vectors are those described in Roth et al. (1996), PCT Application No WO 93/25234, PCT Application No WO 94/06920, Roux et al., 1989, Julan et al., 1992 and Neda et al., 1991.

Yet another viral vector system that is contemplated by the invention consists in the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al., 1992; Samulski et al., 1989; McLaughlin et al., 1989). One advantageous feature of AAV derives from its reduced efficacy for transducing primary cells relative to transformed cells.

Other compositions containing a vector of the invention advantageously comprise an oligonucleotide fragment of the nucleic sequence SEQ ID No 2, preferably a fragment including the start codon of the CIDE B gene, as an anti sense tool that inhibits the expression of the corresponding CIDE B gene. Preferred methods using antisense polynucleotide according to the present invention are the procedures described by Sczakiel et al. (1995) or those described in PCT Application No WO 95/24223.

Preferably, the antisense tools are chosen among the polynucleotides (15–200 bp long) that are complementary to the 5' end of the CIDE B mRNA. In another embodiment, a combination of different antisense polynucleotides complementary to different parts of the desired targeted gene are used.

Preferred antisense polynucleotides according to the present invention are complementary to a sequence of the mRNAs of CIDE B that contains the translation initiation codon ATG.

Host Cells

Another object of the invention consists in host cell that have been transformed or transfected with one of the polynucleotides described therein, and more precisely a polynucleotide either comprising a CIDE B regulatory polynucleotide or the coding sequence of the CIDE B polypeptide having the amino acid sequence of SEQ ID No 3 or fragments or variants thereof. Are included host cells that are transformed (prokaryotic cells) or that are transfected (eukaryotic cells) with a recombinant vector such as one of those described above.

A recombinant host cell of the invention comprises any one of the polynucleotides or the recombinant vectors described therein. More particularly, the cell hosts of the present invention can comprise any of the polynucleotides described in "CIDE B cDNA Sequences" section, the "Coding Regions Of CIDE B" section, "Genomic sequence of CIDE B " section, the "Oligonucleotide Probes And Primers" section and the "Vectors for the expression of a regulatory or coding polynucleotide of CIDE B" section.

Preferred host cells used as recipients for the expression vectors of the invention are the following:

a) Prokaryotic host cells: *Escherichia coli* strains (I.E. DH5-α strain) or *Bacillus subtilis*.
b) Eukaryotic host cells: HeLa cells (ATCC N°CCL2: N°CCL2.1; N°CCL2.2), Cv 1 cells (ATCC N°CCL70), COS cells (ATCC N°CRL1650; N°CRL1651), Sf-9 cells (ATCC N°CRL1711).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skill artisan.

Transgenic Animals

The terms "transgenic animals" or "host animals" are used herein to designate animals that have their genome genetically and artificially manipulated so as to include one of the nucleic acids according to the invention. Preferred animals are non-human mammals and include those belonging to a genus selected from Mus (e.g. mice), Rattus (e.g. rats) and Oryctogalus (e.g. rabbits) which have their genome artificially and genetically altered by the insertion of a nucleic acid according to the invention.

The transgenic animals of the invention all include within a plurality of their cells a cloned recombinant or synthetic DNA sequence, more specifically one of the purified or isolated nucleic acids comprising a CIDE B coding sequence, a CIDE B regulatory polynucleotide or a DNA sequence encoding an antisense polynucleotide such as described in the present specification.

More particularly, transgenic animals according to the invention contain in their somatic cells and/or in their germ line cells any of the polynucleotides described in "CIDEB cDNA Sequences" section, the "Coding Regions Of CIDE B" section, "Genomic sequence of CIDE B" section, the "Oligonucleotide Probes And Primers" section and the "Vectors for the expression of a regulatory or coding polynucleotide of CIDE B" section.

The replacement of the native genomic CIDE B sequence by a defective copy of said sequence may be preformed by techniques of gene targeting. Such techniques are notably described by Burright et al. (1997), Bates et al. (1997), Mangiarini et al. (1997), Davies et al. (1997).

Second preferred transgenic animals of the invention have the murine CIDE B gene replaced either by a defective copy of the murine CIDE B gene or by an interrupted copy of the human CIDE B gene. A "defective copy" of a murine or a human CIDE B gene, is intended to designate a modified copy of these genes that is not or poorly transcribed in the resulting recombinant host animal or a modified copy of these genes leading to the absence of synthesis of the corresponding translation product or alternatively leading to a modified and/or truncated translation product lacking the biological activity of the wild type CIDE B protein. The altered translation product thus contains amino acid modifications, deletions and substitutions. Modifications and deletions may render the naturally occurring gene nonfunctional, thus leading to a "knockout animal". These transgenic animals are critical for the creation of animal models of human diseases, and for eventual treatment of disorders related to apoptosis such as cancer or AIDS. Examples of such knockout mice are described in the PCT Applications Nos WO 97/34641, WO 96/12792 and WO 98/02354.

The endogenous murine CIDE B gene can be interrupted by the insertion, between two contiguous nucleotide of said gene, of a part of all of a marker gene placed under the control of the appropriate promoter, for example the endogenous promoter of the endogenous murine CIDE B gene. The marker gene may be the neomycin resistance gene (neo) that may be operably linked to the phosphoglycerate kinase-1 (PGK-1) promoter, as described in the PCT Application No WO 98/02534.

Thus, the invention is also directed to a transgenic animal contain in their somatic cells and/or in their germ line cells a polynucleotide selected from the following group of polynucleotides:

a) a defective copy of the human CIDE B gene;
b) a defective copy of the endogenous CIDE B gene, wherein the expression "endogenous CIDE B gene" designates a CIDE B gene that is naturally present within the genome of the animal host to be genetically modified.

The invention also concerns a method for obtaining transgenic animals, wherein said methods comprise the steps of:

a) replacing the endogenous copy of the animal CIDE B gene by a nucleic acid selected from the group consisting of a defective copy of the human CIDE B gene and a defective copy of the endogenous CIDE B gene in animal cells, preferably embryonic stem cells (ES);
b) introducing the recombinant animal cells obtained at step a) in embryos, notably blastocysts of the animal;
c) selecting the resulting transgenic animals, for example by detecting the defective copy of a CIDE B gene with one or several primers or probes according to the invention.

Optionally, the transgenic animals may be bred together in order to obtain homozygous transgenic animals for the defective copy of the CIDE B gene introduced.

The transgenic animals of the invention thus contain specific sequences of exogenous genetic material such as the nucleotide sequences described above in detail.

In a first preferred embodiment, these transgenic animals may be good experimental models in order to study the diverse pathologies related to disorders associated to apoptosis, in particular concerning the transgenic animals within the genome of which has been inserted one or several copies of a polynucleotide encoding a native CIDE B protein, or alternatively a mutant CIDE B protein.

In a second preferred embodiment, these transgenic animals may express a desired polypeptide of interest under the control of the regulatory polynucleotides of the CIDE B gene, leading to good yields in the synthesis of this protein of interest, and eventually a tissue specific expression of this protein of interest.

Since it is possible to produce transgenic animals of the invention using a variety of different sequences, a general description will be given of the production of transgenic animals by referring generally to exogenous genetic material. This general description can be adapted by those skilled in the art in order to incorporate the DNA sequences into animals. For more details regarding the production of transgenic animals, and specifically transgenic mice, it may be referred to Sandou et al. (1994) and also to U.S. Pat. No. 4,873,191, issued Oct.10, 1989, U.S. Pat. No. 5,968,766, issued Dec. 16, 1997 and U.S. Pat. No. 5,387,742, issued Feb. 28, 1995.

Transgenic animals of the present invention are produced by the application of procedures which result in an animal with a genome that incorporates exogenous genetic material which is integrated into the genome. The procedure involves obtaining the genetic material, or a portion thereof, which encodes either a CIDE B coding sequence, a CIDE B regulatory polynucleotide or a DNA sequence encoding an antisense polynucleotide such as described in the present specification.

A recombinant polynucleotide of the invention is inserted into an embryonic or ES stem cell line. The insertion is made using electroporation. The cells subjected to electroporation are screened (e.g. Southern blot analysis) to find positive cells which have integrated the exogenous recombinant polynucleotide into their genome. An illustrative positive-negative selection procedure that may be used according to the invention is described by Mansour et al. (1988). Then, the positive cells are isolated, cloned and injected into 3.5 days old blastocysts from mice. The blastocysts are then inserted into a female host animal and allowed to grow to term. The offsprings of the female host are tested to determine which animals are transgenic e.g. include the inserted exogenous DNA sequence and which are wild-type.

Thus, the present invention also concerns a transgenic animal containing a nucleic acid, a recombinant expression vector or a recombinant host cell according to the invention.

Methods for Screening Substances Interacting with a CIDE B Polypeptide

For the purpose of the present invention, a ligand means a molecule, such as a protein, a peptide, an antibody or any synthetic chemical compound capable of binding to the CIDE B protein or one of its fragments or variants or to modulate the expression of the polynucleotide coding for CIDE B or a fragment or variant thereof.

In the ligand screening method according to the present invention, a biological sample or a defined molecule to be tested as a putative ligand of the CIDE B protein is brought into contact with the purified CIDE B protein, for example the purified recombinant CIDE B protein produced by a recombinant cell host as described hereinbefore, in order to form a complex between the CIDE B protein and the putative ligand molecule to be tested.

Another object of the present invention consists of methods and kits for the screening of candidate substances that interact with a CIDE B polypeptide.

The present invention pertains to methods for screening substances of interest that interact with a CIDE B protein or one fragment or variant thereof. By their capacity to bind covalently or non-covalently to a CIDE B protein or to a fragment or variant thereof, these substances or molecules may be advantageously used both in vitro and in vivo.

In vitro, said interacting molecules may be used as detection means in order to identify the presence of a CIDE B protein in a sample, preferably a biological sample.

A method for the screening of a candidate substance interacting with a CIDE B polypeptide of the present invention comprises the following steps:
 a) providing a polypeptide consisting of a CIDE B protein or a fragment or a variant thereof;
 b) obtaining a candidate substance;
 c) bringing into contact said polypeptide with said candidate substance;
 d) detecting the complexes formed between said polypeptide and said candidate substance.

In one embodiment of the screening method defined above, the complexes formed between the polypeptide and the candidate substance are further incubated in the presence of a polyclonal or a monoclonal antibody that specifically binds to the CIDE B protein or to said fragment or variant thereof.

Various candidate substances or molecules can be assayed for interaction with a CIDE B polypeptide. These substances or molecules include, without being limited to, natural or synthetic organic compounds or molecules of biological origin such as polypeptides. When the candidate substance or molecule consists of a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

In another embodiment of the present screening method, increasing concentrations of a monoclonal or polyclonal antibody directed against a CIDE B protein or a fragment or a variant thereof is reacted with the considered CIDE B protein or with a fragment or variant thereof, simultaneously or prior to the addition of the candidate substance or molecule, when performing step c) of said method. By this technique, the detection and optionally the quantification of the complexes formed between the CIDE B protein or the fragment or variant thereof and the substance or molecule to be screened allows the one skilled in the art to determine the affinity value of said substance or molecule for said CIDE B protein or the fragment or variant thereof.

The invention also pertains to kits useful for performing the hereinbefore described screening method. Preferably, such kits comprise a CIDE B polypeptide or a fragment or a variant thereof, and optionally means useful to detect the complex formed between the CIDE B polypeptide or its fragment or variant and the candidate substance. In a preferred embodiment the detection means consist in monoclonal or polyclonal antibodies directed against The CIDE B polypeptide or a fragment or a variant thereof.

1. Candidate Ligands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to 20 amino acids in length (Oldenburg K. R. et al., 1992; Valadon P., et al., 1996; Lucas A. H., 1994; Westerink M. A. J., 1995; Castagnoli L. et al., 1991). According to this particular embodiment, the recombinant phages expressing a protein that binds to the immobilized CIDE B protein is retained and the complex formed between the CIDE B protein and the recombinant phage may be subsequently immunoprecipitated by a polyclonal or a monoclonal antibody directed against the CIDE B protein.

Once the ligand library in recombinant phages has been constructed, the phage population is brought into contact with the immobilized CIDE B protein. Then the preparation of complexes is washed in order to remove the non-specifically bound recombinant phages. The phages that bind specifically to the CIDE B protein are then eluted by a buffer (acid pH) or immunoprecipitated by the monoclonal antibody produced by the hybridoma anti-CIDE B, and this phage population is subsequently amplified by an over-infection of bacteria (for example E. coli). The selection step may be repeated several times, preferably 2–4 times, in order to select the more specific recombinant phage clones. The last step consists in characterizing the peptide produced by the selected recombinant phage clones either by expression in infected bacteria and isolation, expressing the phage insert in another host-vector system, or sequencing the insert contained in the selected recombinant phages.

2. Candidate Ligands Obtained Through a Two-hybrid Screening Assay

The yeast two-hybrid system is designed to study protein-protein interactions in vivo (Fields and Song, 1989), and relies upon the fusion of a bait protein to the DNA binding domain of the yeast Gal4 protein. This technique is also described in the U.S. Pat. Nos. 5,667,973 and 5,283,173 (Fields et al.).

The general procedure of library screening by the two-hybrid assay may be performed as described by Harper et al. (1993) or as described by Cho et al. (1998) or also Fromont-Racine et al. (1997).

The bait protein or polypeptide consists of a CIDE B polypeptide or a fragment or variant thereof.

More precisely, the nucleotide sequence encoding the CIDE B polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non limiting example the two different yeast strains may be the followings:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh');

Y187, the phenotype of which is (MATa gal4 gal80 his3 trp1-901 ade2-101 ura3-52 leu2-3, -112 URA3 GAL-lacZmet), which is the opposite mating type of Y190.

Briefly, 20 μg of pAS2/CIDE B and 20 μg of pACT-cDNA library are co-transformed into yeast strain Y190. The transformants are selected for growth on minimal media lacking histidine, leucine and tryptophan, but containing the histidine stnthesis inhibitor 3-AT (50 mM). Positive colonies are screened for beta galactosidase by filter lift assay. The double positive colonies (His+, beta-gal+) are then grown on plates lacking histidine, leucine, but containing tryptophan and cycloheximide (10 mg/ml) to select for loss of pAS2/CIDE B plasmids bu retention of pACT-cDNA library plasmids. The resulting Y190 strains are mated with Y187 strains expressing CIDE B or non-related control proteins; such as cyclophilin B, lamin, or SNF1, as Gal4 fusions as described by Harper et al. (1993) and by Bram et al. (1993), and screened for beta galactosidase by filter lift assay. Yeast clones that are beta gal- after mating with the control Gal4 fusions are considered false positives.

In another embodiment of the two-hybrid method according to the invention, interaction between CIDE B or a fragment or variant thereof with cellular proteins may be assessed using the Matchmaker Two Hybrid System 2 (Catalog No. K1604-1, Clontech). ). As described in the manual accompanying the Matchmaker Two Hybrid System 2 (Catalog No. K1604-1, Clontech), the disclosure of which is incorporated herein by reference, nucleic acids encoding the RBP-7 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GALA dependent expression of the HIS3 gene. Transformants capable of growing on medium lacking histidine are screened for GAL4 dependent lacZ expression. Those cells which are positive in both the histidine selection and the lacZ assay contain interaction between CIDE B and the protein or peptide encoded by the initially selected cDNA insert.

3. Candidate Ligands Obtained by Affinity Chromatography

Proteins or other molecules interacting with the CIDE B protein, or a fragment thereof can also be found using affinity columns which contain the CIDE B protein, or a fragment thereof. The CIDE B protein, or a fragment thereof, may be attached to the column using conventional techniques including chemical coupling to a suitable column matrix such as agarose, Affi Gel®, or other matrices familiar to those of skill in art. In some embodiments of this method, the affinity column contains chimeric proteins in which the CIDE B protein, or a fragment thereof, is fused to glutathion S transferase (GST). A mixture of cellular proteins or pool of expressed proteins as described above is applied to the affinity column. Proteins or other molecules interacting with the CIDE B protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis based methods and sequenced. The same method can be used to isolate antibodies, to screen phage display products, or to screen phage display human antibodies.

4. Candidate Ligands Obtained by Optical Biosensor Methods

Proteins interacting with the CIDE B protein, or a fragment comprising a contiguous span of at least 6 amino acids, preferably at least 8 to 10 amino acids, more preferably at least 12, 15, 20, 25, 30, 40, 50, or 100 amino acids of SEQ ID No 3, wherein said contiguous span includes at least 1, 2, 3, 5 or 10 of the amino acid positions 7–11, 18–29, 47, 55–63, 70, 103–104, 111–115, 124, 134, 169–173, 181–185, and 203–219, can also be screened by using an Optical Biosensor as described in Edwards and Leatherbarrow (1997) and also in Szabo et al. (1995), the disclosure of which is incorporated by reference. This technique permits the detection of interactions between molecules in real time, without the need of labeled molecules. This technique is based on the surface plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the CIDE B protein, or a fragment thereof, the CIDE B protein, or a fragment thereof, is immobilized onto a surface. This surface comprises one side of a cell through which flows the candidate molecule to be assayed. The binding of the candidate molecule on the CIDE B protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed CIDE B protein at their surface.

The main advantage of the method is that it allows the determination of the association rate between the CIDE B protein and molecules interacting with the CIDE B protein. It is thus possible to select specifically ligand molecules interacting with the CIDE B protein, or a fragment thereof, through strong or conversely weak association constants.

Method for Screening Ligands that Modulate the Expression of the CIDE B Gene

Another subject of the present invention is a method for screening molecules that modulate the expression of the CIDE B protein. Such a screening method comprises the steps of:

a) cultivating a prokaryotic or an eukaryotic cell that has been transfected with a nucleotide sequence encoding the CIDE B protein or a variant or a fragment thereof, placed under the control of its own promoter;

b) bringing into contact the cultivated cell with a molecule to be tested;

c) quantifying the expression of the CIDE B protein or a variant or a fragment thereof.

Using DNA recombination techniques well known by the one skill in the art, the CIDE B protein encoding DNA sequence is inserted into an expression vector, downstream from its promoter sequence. As an illustrative example, the promoter sequence of the CIDE B gene is contained in the 5' regulatory region of CIDE B.

The quantification of the expression of the CIDE B protein may be realized either at the mRNA level or at the protein level. In the latter case, polyclonal or monoclonal antibodies may be used to quantify the amounts of the CIDE B protein that have been produced, for example in an ELISA or a RIA assay.

In a preferred embodiment, the quantification of the CIDE B mRNA is realized by a quantitative PCR amplification of the cDNA obtained by a reverse transcription of the total mRNA of the cultivated CIDE B-transfected host cell, using a pair of primers specific for CIDE B.

The present invention also concerns a method for screening substances or molecules that are able to increase, or in contrast to decrease, the level of expression of the CIDE B gene. Such a method may allow the one skilled in the art to select substances exerting a regulating effect on the expression level of the CIDE B gene and which may be useful as active ingredients included in pharmaceutical compositions for treating patients suffering from deficiencies in the regulation of expression of the CIDE B gene.

Thus, is also part of the present invention a method for the screening of a candidate substance or molecule, said method comprising the following steps:

a) providing a recombinant cell host containing a nucleic acid, wherein said nucleic acid comprises a nucleotide sequence selected from the group consisting of SEQ ID Nos 1 and 2;

b) obtaining a candidate substance, and c) determining the ability of the candidate substance to modulate the expression levels of the nucleotide sequences selected from the group consisting of SEQ ID Nos 1 and 2.

The invention also pertains to kits useful for performing the hereinbefore described screening method. Preferably, such kits comprise a recombinant vector that allows the expression of a nucleotide sequence selected from the group consisting of SEQ ID Nos 1 and 2 or alternatively a recombinant cell host containing such a recombinant vector.

In another embodiment of a method for screening of a candidate substance or molecule that modulated the expression of the CIDE B gene, this method comprises the following steps:

a) providing a recombinant cell host containing a nucleic acid, wherein said nucleic acid comprises the 5' regulatory region of CIDE B or a biologically active fragment or variant thereof located upstream a polynucleotide encoding a detectable protein;

b) obtaining a candidate substance, and c) determining the ability of the candidate substance to modulate the expression levels of the polynucleotide encoding the detectable protein.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the hereinbefore described screening method. Preferably, such kits comprise a recombinant vector comprising the 5' regulatory region of CIDE B or a biologically active fragment or variant thereof located upstream and operably linked to a polynucleotide encoding a detectable protein or the CIDE B protein or a fragment or a variant thereof.

For the design of suitable recombinant vectors useful for performing the screening methods described above, it will be referred to the section of the present specification wherein the preferred recombinant vectors of the invention are detailed.

Expression levels and patterns of CIDE B may be analyzed by solution hybridization with long probes as described in International Patent Application No. WO 97/05277, the entire contents of which are incorporated herein by reference. Briefly, the CIDE B cDNA or the CIDE B genomic DNA described above, or fragments thereof, is inserted at a cloning site immediately downstream of a bacteriophage (T3, T7 or SP6) RNA polymerase promoter to produce antisense RNA. Preferably, the CIDE B insert comprises at least 100 or more consecutive nucleotides of the genomic DNA sequence or the cDNA sequences, particularly those comprising at least one of SEQ ID Nos 15–18 or those encoding mutated CIDE B. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridizations are performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Methods for Inhibiting the Expression of a CIDE B Gene

Other therapeutic compositions according to the present invention comprise advantageously an oligonucleotide fragment of the nucleic sequence of CIDE B as an antisense tool that inhibits the expression of the corresponding CIDE B gene. Preferred methods using antisense polynucleotide according to the present invention are the procedures described by Sczakiel et al. (1995).

Preferably, the antisense tools are chosen among the polynucleotides (15–200 bp long) that are complementary to the 5' end of the CIDE B mRNA. In another embodiment, a combination of different antisense polynucleotides complementary to different parts of the desired targeted gene are used.

Preferred antisense polynucleotides according to the present invention are complementary to a sequence of the mRNAs of CIDE B that contains the translation initiation codon ATG.

The antisense nucleic acid molecules to be used in gene therapy may be either DNA or RNA sequences. They comprise a nucleotide sequence complementary to the targeted sequence of the CIDE B genomic DNA, the sequence of which can be determined using one of the detection methods of the present invention. In a preferred embodiment, the antisense oligonucleotide are able to hybridize with at least one of the splicing sites of the targeted CIDE B gene, or with the 3'UTR of the 5' UTR. The antisense nucleic acids should have a length and melting temperature sufficient to permit formation of an intracellular duplex having sufficient stability to inhibit the expression of the CIDE B mRNA in the duplex. Strategies for designing antisense nucleic acids suitable for use in gene therapy are disclosed in Green et al., (1986) and Izant and Weintraub, (1984).

In some strategies, antisense molecules are obtained by reversing the orientation of the CIDE B coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of CIDE B antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2

An alternative to the antisense technology that is used according to the present invention consists in using ribozymes that will bind to a target sequence via their complementary polynucleotide tail and that will cleave the corresponding RNA by hydrolyzing its target site (namely (<<hammerhead ribozymes>>). Briefly, the simplified cycle of a hammerhead ribozyme consists of (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995).

Throughout this application, various publications, patents and published patent applications are cited. The disclosures of these publications, patents and published patent specification referenced in this application are hereby incorporated by reference into the present disclosure to more fully describe the sate of the art to which this invention pertains.

EXAMPLES

Example 1

Identification of Biallelic Markers—DNA Extraction

Donors were unrelated and healthy. They presented a sufficient diversity for being representative of a French heterogeneous population. The DNA from 100 individuals was extracted and tested for the detection of the biallelic markers.

30 ml of peripheral venous blood were taken from each donor in the presence of EDTA. Cells (pellet) were collected after centrifugation for 10 minutes at 2000 rpm. Red cells were lysed by a lysis solution (50 ml final volume: 10 nM Tris pH 7.6;5 nM $MgCl_2$; 10 nM NaCl). The solution was centrifuged (10 minutes, 2000 rpm) as many times as necessary to eliminate the residual red cells present in the supernatant, after resuspension of the pellet in the lysis solution.

The pellet of white cells was lysed overnight at 42° C. with 3.7 ml of lysis solution composed of:

3 ml TE 10-2 (Tris-HCl 10 mM, EDTA 2 mM)/NaCl 0 4 M

200 µl SDS 10%

500 µl K-proteinase (2 mg K-proteinase in TE 10-2/NaCl 0.4 M).

For the extraction of proteins, 1 ml saturated NaCl (6M) (1/3.5 v/v) was added. After vigorous agitation, the solution was centrifuged for 20 minutes at 10000 rpm.

For the precipitation of DNA, 2 to 3 volumes of 100% ethanol were added to the previous supernatant, and the solution was centrifuged for 30 minutes at 2000 rpm. The DNA solution was rinsed three times with 70% ethanol to eliminate salts, and centrifuged for 20 minutes at 2000 rpm. The pellet was dried at 37° C., and resuspended in 1 ml TE 10-1 or 1 ml water. The DNA concentration was evaluated by measuring the OD at 260 nm (1 unit OD=50 µg/ml DNA).

To determine the presence of proteins in the DNA solution, the OD 260/OD 280 ratio was determined. Only DNA preparations having a OD 260/OD 280 ratio between 1.8 and 2 were used in the subsequent examples described below.

The pool was constituted by mixing equivalent quantities of DNA from each individual.

Example 2

Identification of Biallelic Markers: Amplification of Genomic DNA by PCR

The amplification of specific genomic sequences of the DNA samples of example 1 was carried out on the pool of DNA obtained previously. In addition, 50 individual samples were similarly amplified.

PCR assays were performed using the following protocol:

| | |
|---|---|
| Final volume | 25 µl |
| DNA | 2 ng/µl |
| $MgCl_2$ | 2 mM |
| dNTP (each) | 200 µM |
| primer (each) | 2.9 ng/µl |
| Ampli Taq Gold DNA polymerase | 0.05 unit/µl |
| PCR buffer (10x = 0.1 M TrisHCl pH8.3 0.5 M KCl) | 1 x |

Each pair of first primers was designed using the sequence information of the CIDE B gene disclosed herein and the OSP software (Hillier & Green, 1991). This first pair of primers was about 20 nucleotides in length and had the sequences disclosed in Table 1 in the columns labeled PU and RP.

TABLE 1

| Amplicon | Position range of the amplicon in SEQ ID 1 | | Primer name | Position range of amplification primer in SEQ ID No 1 | | Primer name | Complementary position range of amplification primer in SEQ ID NO 1 | |
|---|---|---|---|---|---|---|---|---|
| 12-73 | 6704 | 7169 | B(12-73) | 6704 | 6723 | C(12-73) | 7152 | 7169 |
| 12-74 | 9538 | 9988 | B(12-74) | 9538 | 9557 | C(12-74) | 9970 | 9988 |

Preferably, the primers contained a common oligonucleotide tail upstream of the specific bases targeted for amplification which was useful for sequencing.

Primers PU contain the following additional PU 5' sequence:
TGTAAAACGACGGCCAGT; primers RP contain the following RP 5' sequence: CAGGAAACAGCTATGACC. The primer containing the additional PU 5' sequence is listed in SEQ ID No 4. The primer containing the additional RP 5' sequence is listed in SEQ ID No 5.

The synthesis of these primers was performed following the phosphoramidite method, on a GENSET UFPS 24.1 synthesizer.

DNA amplification was performed on a Genius II thermocycler. After heating at 95° C. for 10 min, 40 cycles were performed. Each cycle comprised: 30 sec at 95° C., 54° C. for 1 min, and 30 sec at 72° C. For final elongation, 10 min at 72° C. ended the amplification. The quantities of the amplification products obtained were determined on 96-well microtiter plates, using a fluorometer and Picogreen as intercalant agent (Molecular Probes).

Example 3

Identification of Biallelic Markers—Sequencing of Amplified Genomic DNA and Identification of Polymorphisms The sequencing of the amplified DNA obtained in example 2 was carried out on ABI 377 sequencers. The sequences of the amplification products were determined using automated dideoxy terminator sequencing reactions with a dye terminator cycle sequencing protocol. The products of the sequencing reactions were run on sequencing gels and the sequences were determined using gel image analysis (ABI Prism DNA Sequencing Analysis software (2.1.2 version)).

The sequence data were further evaluated to detect the presence of biallelic markers within the amplified fragments. The polymorphism search was based on the presence of superimposed peaks in the electrophoresis pattern resulting from different bases occurring at the same position as described previously.

In the 2 fragments of amplification, 2 biallelic markers were detected. The localization of these biallelic markers are as shown in Table 2.

TABLE 2

| Amplicon | Marker Name | Localization in CIDE B gene | Polymorphism allele1 | Polymorphism allele2 | BM position in SEQ ID No 1 |
|---|---|---|---|---|---|
| 12-73 | 12-73-49 | 3' regulatory region | C | T | 7123 |
| 12-74 | 12-74-38 | 3' regulatory region | C | T | 9574 |

TABLE 3

| Marker Name | Position range of probes in SEQ ID No 1 | | Probes |
|---|---|---|---|
| 12-73-49 | 7100 | 7146 | P(12-73-49) |
| 12-74-38 | 9551 | 9597 | P(12-74-38) |

Example 4

Validation of the Polymorphisms Through Microsequencing

The biallelic markers identified in example 3 were further confirmed and their respective frequencies were determined through microsequencing. Microsequencing was carried out for each individual DNA sample described in Example 1.

Amplification from genomic DNA of individuals was performed by PCR as described above for the detection of the biallelic markers with the same set of PCR primers (Table 1), The preferred primers used in microsequencing were about 19 nucleotides in length and hybridized just upstream of the considered polymorphic base. According to the invention, the primers used in microsequencing are detailed in Table 4.

TABLE 4

| Marker Name | Mis. 1 | Position range of microsequencing primer mis 1 in SEQ ID No 1 | | Mis. 2 | Complementary postion range of microsequencing primer mis. 2 in SEQ ID No 1 | |
|---|---|---|---|---|---|---|
| 12-73-49 | D(12-73-49) | 7104 | 7122 | E(12-73-49) | 7124 | 7142 |
| 12-74-38 | D(12-74-38) | 9555 | 9573 | E(12-74-38) | 9575 | 9593 |

Mis 1 and Mis 2 respectively refer to microsequencing primers which hybridized with the non-coding strand of the CIDE B gene or with the coding strand of the CIDE B gene.

The microsequencing reaction was performed as follows:

After purification of the amplification products, the microsequencing reaction mixture was prepared by adding, in a 20 μl final volume: 10 pmol microsequencing oligonucleotide, 1 mU Thermosequenase (Amersham E79000G), 1.25 μl Thermosequenase buffer (260 MM Tris HCl pH 9.5, 65 mM $MgCl_2$), and the two appropriate fluorescent ddNTPs (Perkin Elmer, Dye Terminator Set 401095) complementary to the nucleotides at the polymorphic site of each biallelic marker tested, following the manufacturer's recommendations. After 4 minutes at 94° C., 20 PCR cycles of 15 sec at 55° C., 5 sec at 72° C., and 10 sec at 94° C. were carried out in a Tetrad PTC-225 thermocycler (MJ Research). The unincorporated dye terminators were then removed by ethanol precipitation. Samples were finally resuspended in formamide-EDTA loading buffer and heated for 2 min at 95° C. before being loaded on a polyacrylamide sequencing gel. The data were collected by an ABI PRISM 377 DNA sequencer and processed using the GENESCAN software (Perkin Elmer).

Following gel analysis, data were automatically processed with software that allows the determination of the alleles of biallelic markers present in each amplified fragment.

The software evaluates such factors as whether the intensities of the signals resulting from the above microsequencing procedures are weak, normal, or saturated, or whether the signals are ambiguous. In addition, the software identifies significant peaks (according to shape and height criteria). Among the significant peaks, peaks corresponding to the targeted site are identified based on their position. When two significant peaks are detected for the same position each sample is categorized classification as homozygous or heterozygous type based on the height ratio.

Example 5

Preparation of Antibody Compositions to the CIDE B Protein

Substantially pure protein or polypeptide is isolated from transfected or transformed cells containing an expression vector encoding the CIDE B protein or a portion thereof. The concentration of protein in the final preparation is adjusted, for example, by concentration on an Amicon filter device, to the level of a few micrograms/ml. Monoclonal or polyclonal antibody to the protein can then be prepared as follows:

A. Monoclonal Antibody Production by Hybridoma Fusion

Monoclonal antibody to epitopes in the CIDE B protein or a portion thereof can be prepared from murine hybridomas according to the classical method of Kohler, G. and Milstein, C., (1975) or derivative methods thereof. Also see Harlow, E., and D. Lane. 1988.

Briefly, a mouse is repetitively inoculated with a few micrograms of the CIDE B protein or a portion thereof over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, New York. Section 21-2.

B. Polyclonal Antibody Production by Immunization

Polyclonal antiserum containing antibodies to heterogeneous epitopes in the CIDE B protein or a portion thereof can be prepared by immunizing suitable non-human animal with the CIDE B protein or a portion thereof, which can be unmodified or modified to enhance immunogenicity. A suitable non-human animal is preferably a non-human mammal is selected, usually a mouse, rat, rabbit, goat, or horse. Alternatively, a crude preparation which has been enriched for CIDE B concentration can be used to generate antibodies. Such proteins, fragments or preparations are introduced into the non-human mammal in the presence of an appropriate adjuvant (e.g. aluminum hydroxide, RIBI, etc.) which is known in the art. In addition the protein, fragment or preparation can be pretreated with an agent which will increase antigenicity, such agents are known in the art and include, for example, methylated bovine serum albumin (mBSA), bovine serum albumin (BSA), Hepatitis B surface antigen, and keyhole limpet hemocyanin (KLH). Serum from the immunized animal is collected, treated and tested according to known procedures. If the serum contains polyclonal antibodies to undesired epitopes, the polyclonal antibodies can be purified by immunoaffinity chromatography.

Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. Techniques for producing and processing polyclonal antisera are known in the art, see for example, Mayer and Walker (1987). An effective immunization protocol for rabbits can be found in Vaitukaitis, J. et al. (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., (1980).

Antibody preparations prepared according to either the monoclonal or the polyclonal protocol are useful in quantitative inmnunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

While the preferred embodiment of the invention has been illustrated and described, it will be appreciated that various changes can be made therein by the one skilled in the art without departing from the spirit and scope of the invention.

REFERENCES

Altschul et al., 1990, J. Mol. Biol. 215(3):403–410/ Altschul et al., 1993, Nature Genetics 3:266–272/Altschul et al., 1997, Nuc. Acids Res. 25:3389–3402/Ausubel et al. (1989)Current Protocols in Molecular Biology, Green Publishing Associates and Wiley lnterscience, N.Y./Bates G P et al., 1997a, Hum. Mol. Genet., 6(10):1633–1637./Bates G P et al., 1997b, Molecular Medicine today, November 1997, 508:515./Beaucage et al., Tetrahedron Lett 1981, 22: 1859–1862/Bram R J et al., 1993, Mol. Cell Biol., 13:4760–4769/Brown E L, et al., Methods Enzymol 1979;68:109–151/Burright et al., 1997, Brain Pathology, 7:965–977./Castagnoli L. et al. (Felici F.), 1991, J. Mol. Biol., 222:301–310/Chai H. et al. (1993) Biotechnol. Appl. Biochem.18:259–273./Chee et al. (1996) Science. 274:610–614./Chen and Kwok Nucleic Acids Research 25:347–353 1997/Chen et al. Proc. Natl. Acad. Sci. USA 94/20 10756–10761,1997/Cho R J et al., 1998, Proc. Natl. Acad. Sci. USA, 95(7): 3752–3757./Coles R, et al., Hum Mol Genet 1998;7(5):791–800/Compton J. (1991) Nature. 350 (6313):91–92./Davies S W, et al. Cell 1997;90(3):53748/ Edwards et Leatherbarrow, Analytical Biochemistry, 246, 1–6 (1997)/Engvall, E., Meth. Enzymol. 70:419 (1980)/ Feldman and Steg, 1996, Medecine/Sciences, synthese, 12:47–55/Fields and Song, 1989, Nature, 340:245–246/ Fisher, D., Chap. 42 in: Manual of Clinical Immunology, 2d Ed. (Rose and Friedman, Eds.) Amer. Soc. For Microbiol., Washington, D.C. (1980)/Flotte et al., 1992, Am. J. Respir. Cell Mol. Biol., 7: 349–356./Fodor et al. (1991) Science 251:767–777./Fromont-Racine M. et al., 1997, Nature Genetics, 16(3): 277–282./Fuller S. A. et al. (1996) Immunology in Current Protocols in Molecular Biology, Ausubel et al. Eds, John Wiley & Sons, Inc., USA./Geysen H. Mario et al. 1984. Proc. Natl. Acad. Sci. U.S.A. 81:3998–4002/ Gonnet et al., 1992, Science 256:1443–1445/Green et al., Ann. Rev. Biochem. 55:569–597 (1986)/Grompe, M. (1993) Nature Genetics. 5:111–117./Grompe, M. et al. (1989) Proc. Natl. Acad. Sci. U.S.A. 86:5855–5892./Guatelli J C et al. Proc. Natl. Acad. Sci. USA. 35:273–286./Hacia J G, et al., Nat Genet 1996;14(4):441–447/Haff L. A. and Smirnov I. P. (1997) Genome Research, 7:378–388./Hames B. D. and Higgins S. J. (1985) Nucleic Acid Hybridization: A Practical Approach. Hames and Higgins Ed., IRL Press, Oxford./ Harju L, et al., Clin Chem 1993;39(11Pt 1):2282–2287/ Harlow, E., and D. Lane. 1988. Antibodies A Laboratory Manual. Cold Spring Harbor Laboratory. pp. 53–242/Harper J W et al., 1993, Cell, 75:805–816 /Henikoff and Henikoff, 1993, Proteins 17:49–61/Higgins et al., 1996, Methods Enzymol. 266:383–402/Hillier L. and Green P. *Methods Appl.*, 1991, 1:124–8./Huang L. et al. (1996) *Cancer Res* 56(5):1137–1141./Huygen et al. (1996) *Nature Medicine.* 2(8):893–898./Inohara N. et al., 1998, *The EMBO J.*, 17(9),: 2526–2533./Izant J G, Weintraub H, *Cell* April 1984;36(4): 1007–15/Julan et al., 1992 *J. Gen. Virol.*, 73:3251–3255./ Karlin and Altschul, 1990, Proc. Natl. Acad. Sci. USA 87:2267–2268/Kohler, G. and Milstein, C., Nature 256:495 (1975)/Kozal M J, et al., Nat Med 1996;2(7):753–759/ Landegren U. et al. (1998) *Genome Research*, 8:769–776./ Leger O J, et al., 1997, *Hum Antibodies*, 8(1): 3–16/Lenhard T. et al. (1996) *Gene.* 169:187–190./Lin M W et al., 1997, *Hum. Genet.*, 99(3): 417420./Livak et al., *Nature Genetics*, 9:341–342, 1995/Livak K J, Hainer J W, *Hum Mutat* 1994;3 (4):379–385/Lucas A. H., 1994, In: Development and Clinical Uses of Haempophilus b Conjugate;/Mackey K, et al., 1998, *Mol Biotechnol*, 9(1):1–5/Mangiarini L, et al. *Nat Genet* February 1997;15(2):197–200/Mansour S L et al., 1988, Nature, 336: 348–352./Marshall R. L. et al. (1994) *PCR Methods and Applications.* 4:80–84./Martineau P, et al., 1998, *J Mol Biol*, 280(1):117–127/McLaughlin B A et al., 1996,*Am. J Hum. Genet.*, 59: 561–569./Muzyczka et al., 1992, *Curr. Topics in Micro. and Immunol.*, 158: 97–129./ Narang S A, et al., Methods Enzymol 1979;68:90–98/ Nedaetal., 1991, *J. Biol. Chem.*, 266: 14143–14146./ Nickerson D. A. et al. (1990) *Proc. Natl. Acad. Sci. U.S.A.* 87:8923–8927./Nyren P, et al., *Anal Biochem* 1993;208(1): 171–175/O'Reilly et al. (1992) *Baculovirus Expression Vectors: A Laboratory Manual.* W. H. Freeman and Co., New York./Ohno et al. (1994) *Science.* 265:781–784./Oldenburg K. R. et al., 1992, *Proc. Natl. Acad. Sci.*, 89:5393–5397./ Orita et al. (1989) *Proc. Natl. Acad. Sci. U.S.A.*86:2776–2770./Ouchterlony, O. et al., Chap. 19 in: Handbook of Experimental Immunology D. Wier (ed) Blackwell (1973)/Parmley and Smith, *Gene,* 1988, 73:305–318/Pastinen et al., *Genome Research* 1997; 7:606–614/Pearson and Lipman, 1988, Proc. Natl. Acad. Sci. USA 85(8):2444–2448/Porath et al., Nature Dec. 18, 1975; 258(5536):598–9/Ramunsen et al., 1997, Electrophoresis, 18:588–598./Reimann K A, et al., 1997, *AIDS Res Hum Retroviruses.* 13(11): 933–943/Ridder R, et al., 1995, *Biotechnology* (NY), 13(3):255–260/Rossi et al., *Pharmacol. Ther.* 50:245–254, (1991)/Roth J. A. et al., 1996, *Nature Medicine,* 2(9):985–991/Rougeot, C. et al.,. *Eur. J. Biochem.* 219 (3): 765–773, 1994/Roux et al., 1989, *Proc. Natl Acad. Sci. USA,* 86: 9079–9083./Sambrook, J., et al., (1989) *Molecular Cloning: A Laboratory Manual.* 2ed. Cold Spring Harbor Laboratory, Cold Spring Harbor, N.Y./ Samson M, et al. (1996) *Nature,* 382(6593):722–725./ Samulski et al., 1989, *J. Virol.,* 63: 3822–3828./Sanchez-Pescador R. (1988) *J. Clin. Microbiol.* 26(10):1934–1938./ Sandou et al., 1994, *Science,* 265: 1875–1878./Schwartz and Dayhoff, eds., 1978, Matrices for Detecting Distance Relationships: Atlas of Protein Sequence and Structure, Washington: National Biomedical Research Foundation/Sczakiel G. et al., 1995, *Trends Microbiol.,* 1995, 3(6):213–217/ Sheffield, V. C. et al. (1991) *Proc. Natl. Acad. Sci. U.S.A.* 49:699–706./Shoemaker D D, et al., *Nat Genet* 1996;14(4): 450–456/Smith et al. (1983) *Mol. Cell. Biol.* 3:2156–2165./ Stryer, L., *Biochemistry,* 4th edition, 1995/Syvanen A C, *Clin Chim Acta* 1994;226(2):225–236/Szabo A. et al. *Curr Opin Struct Biol* 5, 699–705 (1995)/Tacson et al. (1996) *Nature Medicine.* 2(8):888–892./Thompson et al., 1994, Nucleic Acids Res. 22(2):4673–4680/Tyagi et al. (1998) *Nature Biotechnology.* 16:49–53./Urdea M. S. (1988) *Nucleic Acids Research.* 11:4937–4957./Urdea M. S. et al. (1991) *Nucleic Acids Symp. Ser.* 24:197–200./Vaitukaitis, J. et al. J. Clin. Endocrinol. Metab. 33:988–991 (1971)/ Valadon P., et al., 1996, *J. Mol. Biol.,* 261:11–22./Vaughan T J, et al., 1996, *Nat Biotechnol.* 14(3):309–314/Viasak R. et al. (1983) *Eur. J. Biochem.* 135:123–126./Wabiko et al. (1986) *DNA.*5(4):305–314./Walker et al. (1996) *Clin. Chem.* 42:9–13./Wanker E E, Mangiarini L, Bates G P *Cell* 1997;90 (3):537–48/Westerink M. A. J., 1995, *Proc. Nail. Acad. Sci.,* 92:4021–4025/White, M. B. et al. (1992) *Genomics.* 12:301–306./White, M. B. et al. (1997) *Genomics.* 12:301–306.

Sequence Listing Free Text

The following free text appears in the accompanying sequence listing:

5' regulatory region
3' regulatory region
5 polymorphic base or
complement
probe
homology with 5' EST in ref
sequencing oligonucleotide primer

What is claimed:

1. An isolated recombinant polynucleotide, wherein said polynucleotide comprises a nucleotide sequence consisting of SEQ ID NO:1, wherein nucleotide position 7123 of SEQ ID NO:1 is a T and nucleotide position 9574 of SEQ ID NO:1 is a C.

2. An isolated polynucleotide, comprising a nucleic acid sequence selected from the group consisting of:
   a) SEQ ID NO: 1;
   b) SEQ ID NO: 2; and
   c) a nucleotide sequence encoding the human polypeptide of SEQ ID NO: 3.

3. The polynucleotide of claim 2 wherein the nucleotide sequence is a).

4. A recombinant host cell comprising the polynucleotide of claim 3.

5. A method of making a polypeptide encoded by the polynucleotide of claim 3, said method comprising the steps of:
   a) providing a population of host cells comprising said polynucleotide;
   b) culturing said population of host cells under conditions conducive to the production of said polypeptide within said host cells; and
   c) isolating and purifying said polypeptide from said population of host cells.

6. The polynucleotide of claim 2, wherein the nucleotide sequence is b).

7. A recombinant host cell comprising the polynucleotide of claim 4.

8. A method of making a polypeptide encoded by the polynucleotide of claim 4, said method comprising the steps of:
   a) providing a population of host cells comprising said polynucleotide;
   b) culturing said population of host cells under conditions conducive to the production of said polypeptide within said host cells; and
   c) isolating and purifying said polypeptide from said population of host cells.

9. The polynucleotide of claim 2, wherein the nucleotide sequence is c).

10. A recombinant host cell comprising the polynucleotide of claim 9.

11. A method of making a polypeptide encoded by the polynucleotide of claim 9, said method comprising the steps of:
   a) providing a population of host cells comprising said polynucleotide;
   b) culturing said population of host cells under conditions conducive to the production of said polypeptide within said host cells; and
   c) isolating and purifying said polypeptide from said population of host cells.

12. An isolated polynucleotide, consisting of a nucleic acid sequence selected from the group consisting of:
   a) nucleotide positions 2803–2922 of SEQ ID NO: 1;
   b) nucleotide positions 3225–3369 of SEQ ID NO: 1;
   c) nucleotide positions 4603–4793 of SEQ ID NO: 1;
   d) nucleotide positions 1–2802 of SEQ ID NO: 1;
   e) nucleotide positions 80–739 of SEQ ID NO: 2;
   f) a nucleotide sequence encoding a contiguous span of at least 35 amino acids of SEQ ID NO: 3;
   g) a nucleotide sequence encoding a contiguous span of at least 40 amino acids of SEQ ID NO: 3;
   h) a nucleotide sequence encoding a contiguous span of at least 50 amino acids of SEQ ID NO: 3;
   i) a nucleotide sequence encoding a contiguous span of at least 100 amino acids of SEQ ID NO: 3;

j) a nucleotide sequence encoding a contiguous span of at least 200 amino acids of SEQ ID NO: 3;
k) a nucleotide sequence encoding amino acid positions 1–29 of SEQ ID NO: 3;
l) a nucleotide sequence encoding amino acid positions 47–70 of SEQ ID NO: 3;
m) a nucleotide sequence encoding amino acid positions 169–185 of SEQ ID NO: 3;
n) a nucleotide sequence consisting of a contiguous span of at least 12 nucleotides between positions 1–1000 of SEQ ID NO: 1;
o) a nucleotide sequence consisting of a contiguous span of at least 20 nucleotides between positions 1–1000 of SEQ ID NO: 1;
p) a nucleotide sequence consisting of a contiguous span of at least 30 nucleotides between positions 1–1000 of SEQ ID NO: 1;
q) a nucleotide sequence consisting of a contiguous span of at least 50 nucleotides between positions 1–1000 of SEQ ID NO: 1;
r) a nucleotide sequence consisting of a contiguous span of at least 70 nucleotides between positions 1–1000 of SEQ ID NO; 1;
s) a nucleotide sequence consisting of a contiguous span of at least 90 nucleotides between positions 1–1000 of SEQ ID NO: 1; and
t) a nucleotide sequence consisting of a contiguous span of at least 100 nucleotides between positions 1–1000 of SEQ ID NO: 1.

13. The polynucleotide of claim 12, wherein the nucleotide sequence is a).

14. A polynucleotide consisting of a recombinant vector and the nucleic acid of claim 13.

15. A method of making a polypeptide encoded by the polynucleotide of claim 13 or 14, said method comprising the steps of:
   a) providing a population of host cells comprising the polynucleotide of claim 13 or 14;
   b) culturing said population of host cells under conditions conducive to the production of said polypeptide within said host cells; and
   c) isolating and purifying said polypeptide from said population of host cells.

16. A recombinant host cell comprising the polynucleotide of claim 13.

17. The polynucleotide of claim 12, wherein the nucleotide sequence is b).

18. A polynucleotide consisting of a recombinant vector and the nucleic acid of claim 17.

19. A method of making a polypeptide encoded by the polynucleotide of claim 17 or 18, said method comprising the steps of:
   a) providing a population of host cells comprising the polynucleotide of claim 17 or 18;
   b) culturing said population of host cells under conditions conducive to the production of said polypeptide within said host cells; and
   c) isolating and purifying said polypeptide from said population of host cells.

20. A recombinant host cell comprising the polynucleotide of claim 17.

21. The polynucleotide of claim 12, wherein the nucleotide sequence is c).

22. A polynucleotide consisting of a recombinant vector and the nucleic acid of claim 21.

23. A method of making a polypeptide encoded by the polynucleotide of claim 21 or 22, said method comprising the steps of:
   a) providing a population of host cells comprising the polynucleotide of claim 21 or 22;
   b) culturing said population of host cells under conditions conducive to the production of said polypeptide within said host cells; and
   c) isolating and purifying said polypeptide from said population of host cells.

24. A recombinant host cell comprising the polynucleotide of claim 21.

25. The polynucleotide of claim 12, wherein the nucleotide sequence is d).

26. The polynucleotide of claim 12, wherein the nucleotide sequence is e).

27. A polynucleotide consisting of a recombinant vector and the nucleic acid of claim 26.

28. A method of making a polypeptide encoded by the polynucleotide of claim 26 or 27, said method comprising the steps of:
   a) providing a population of host cells comprising the polynucleotide of claim 26 or 27;
   b) culturing said population of host cells under conditions conducive to the production of said polypeptide within said host cells; and
   c) isolating and purifying said polypeptide from said population of host cells.

29. A recombinant host cell comprising the polynucleotide of claim 26.

30. The polynucleotide of claim 12, wherein the nucleotide sequence is f).

31. A polynucleotide consisting of a recombinant vector and the nucleic acid of claim 30.

32. A method of making a polypeptide encoded by the polynucleotide of claim 30 or 31, said method comprising the steps of:
   a) providing a population of host cells comprising the polynucleotide of claim 30 or 31;
   b) culturing said population of host cell under conditions conducive to the production of said polypeptide within said host cells; and
   c) isolating and purifying said polypeptide from said population of host cells.

33. A recombinant host cell comprising the polynucleotide of claim 30.

34. The polynucleotide of claim 12, wherein the nucleotide sequence is g).

35. A polynucleotide consisting of a recombinant vector and the nucleic acid of claim 34.

36. A method of making a polypeptide encoded by the polynucleotide of claim 34 or 35, said method comprising the steps of:
   a) providing a population of host cells comprising the polynucleotide of claim 34 or 35;
   b) culturing said population of host cells under conditions conducive to the production of said polypeptide within said host cells; and
   c) isolating and purifying said polypeptide from said population of host cells.

37. A recombinant host cell comprising the polynucleotide of claim 34.

38. The polynucleotide of claim 12, therein the nucleotide sequence is h).

39. A polynucleotide consisting of a recombinant vector and the nucleic acid of claim 38.

40. A method of making a polypeptide encoded by the polynucleotide of claim 38 or 39, said method comprising the steps of:
a) providing a population of host cells comprising the polynucleotide of claim 38 or 39;
b) culturing said population of host cells under conditions conducive to the production of said polypeptide within said host cells; and
c) isolating and purifying said polypeptide from said population of host cells.

41. A recombinant host cell comprising the polynucleotide of claim 38.

42. The polynucleotide of claim 12, wherein the nucleotide sequence is i).

43. A polynucleotide consisting of a recombinant vector and the nucleic acid of claim 42.

44. A method of making a polypeptide encoded by the polynucleotide of claim 42 or 43, said method comprising the steps of:
a) providing a population of host cells comprising the polynucleotide of claim 42 or 43;
b) culturing said population of host cells under conditions conducive to the production of said polypeptide within said host cells; and
c) isolating and purifying said polypeptide from said population of host cells.

45. A recombinant host cell comprising the polynucleotide of claim 42.

46. The polynucleotide of claim 12, wherein the nucleotide sequence is j).

47. A polynucleotide consisting of a recombinant vector and the nucleic acid of claim 46.

48. A method of making a polypeptide encoded by the polynucleotide of claim 46 or 47, said method comprising the steps of:
a) providing a population of host cells comprising the polynucleotide of claim 46 or 47;
b) culturing said population of host cells under conditions conducive to the production of said polypeptide within said host cells; and
c) isolating and purifying said polypeptide from said population of host cells.

49. A recombinant host cell comprising the polynucleotide of claim 46.

50. The polynucleotide of claim 12, wherein the nucleotide sequence is k).

51. A polynucleotide consisting of a recombinant vector and the nucleic acid of claim 50.

52. A method of making a polypeptide encoded by the polynucleotide of claim 50 or 51, said method comprising the steps of:
a) providing a population of host cells comprising the polynucleotide of claim 50 or 51;
b) culturing said population of host cells under conditions conducive to the production of said polypeptide within said host cells; and
c) isolating and purifying said polypeptide from said population of host cells.

53. A recombinant host cell comprising the polynucleotide of claim 50.

54. The polynucleotide of claim 12, wherein the nucleotide sequence is l).

55. A polynucleotide consisting of a recombinant vector and the nucleic acid of claim 54.

56. A method of making a polypeptide encoded by the polynucleotide of claim 54 or 55, said method comprising the steps of:
a) providing a population of host cells comprising the polynucleotide of claim 54 or 55;
b) culturing said population of host cells under conditions conducive to the production of said polypeptide within said host cells; and
c) isolating and purifying said polypeptide from said population of host cells.

57. A recombinant host cell comprising the polynucleotide of claim 54.

58. The polynucleotide of claim 12, wherein the nucleotide sequence is m).

59. A polynucleotide consisting of a recombinant vector and the nucleic acid of claim 58.

60. A method of making a polypeptide encoded by the polynucleotide of claim 58 or 59, said method comprising the steps of:
a) providing a population of host cells comprising the polynucleotide of claim 58 or 59;
b) culturing said population of host cells under conditions conducive to the production of said polypeptide within said host cells; and
c) isolating and purifying said polypeptide from said population of host cells.

61. A recombinant host cell comprising the polynucleotide of claim 58.

62. The polynucleotide of claim 12, wherein the nucleotide sequence is n).

63. The polynucleotide of claim 12, wherein the nucleotide sequence is o).

64. The polynucleotide of claim 12, wherein the nucleotide sequence is p).

65. The polynucleotide of claim 12, wherein the nucleotide sequence is q).

66. The polynucleotide of claim 12, wherein the nucleotide sequence is r).

67. The polynucleotide of claim 12, wherein the nucleotide sequence is s).

68. The polynucleotide of claim 12, wherein the nucleotide sequence is t).

* * * * *

UNITED STATES PATENT AND TRADEMARK OFFICE
CERTIFICATE OF CORRECTION

PATENT NO. : 6,472,517 B1  Page 1 of 1
DATED : October 29, 2002
INVENTOR(S) : Lydie Bougueleret It is certified that error appears in the above-identified patent and that said Letters Patent is hereby corrected as shown below:

Column 12,
Line 21, "4717" should read -- 4217 --.

Column 22,
Line 10, "sequences of of P(12-73-49)" should read -- sequences of P(12-73-49) --.

Column 23,
Line 41, "D(12-74-38), E(12-73-49), E(12-73-49), and" should read
-- D(12-74-38), E(12-73-49), and --.

Column 25,
Line 50, "One the polypeptides" should read -- One of the polypeptides --.

Column 42,
Lines 36-39, "(ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711)." should read -- (ATCC No. CCL2; No. CCL2.1; No. CCL2.2), Cv 1 cells (ATCC No. CCL70), COS cells (ATCC No. CRL1650; No. CRL1651), Sf-9 cells (ATCC No. CRL1711). --.

Column 47,
Line 19, "the histidine stnthesis inhibitor" should read -- the histidine synthesis inhibitor --.
Line 49, "as well as GALA dependent" should read -- as well as GAL4 dependent --.

Signed and Sealed this

Sixteenth Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,472,517 B1
DATED : October 29, 2002
INVENTOR(S) : Lydie Bougueleret It is certified that error appears in the above-identified patent and that said Letters Patent is hereby corrected as shown below:

Title page,
Item [86], PCT No:, "PCT/IB89/01702" should read -- PCT/IB99/01702 --.

Signed and Sealed this

Twenty-eighth Day of September, 2004

JON W. DUDAS
*Director of the United States Patent and Trademark Office*